(12) United States Patent
Levy et al.

(10) Patent No.: US 8,372,158 B2
(45) Date of Patent: Feb. 12, 2013

(54) OBESITY TREATMENT AND DEVICE

(75) Inventors: Michael J. Levy, Rochester, MN (US); Michael L. Camilleri, Rochester, MN (US); Joseph A. Murray, Rochester, MN (US); William J. Sandborn, Rochester, MN (US)

(73) Assignee: EnteroMedics, Inc., St. Paul, MN (US)

( * ) Notice: Subject to any disclaimer, the term of this patent is extended or adjusted under 35 U.S.C. 154(b) by 322 days.

(21) Appl. No.: 12/887,714

(22) Filed: Sep. 22, 2010

(65) Prior Publication Data

US 2011/0009980 A1 Jan. 13, 2011

Related U.S. Application Data

(63) Continuation of application No. 11/141,869, filed on May 31, 2005, now Pat. No. 7,803,195.

(60) Provisional application No. 60/576,826, filed on Jun. 3, 2004, provisional application No. 60/589,429, filed on Jul. 20, 2004, provisional application No. 60/603,705, filed on Aug. 23, 2004, provisional application No. 60/612,088, filed on Sep. 22, 2004.

(51) Int. Cl.
*A61M 5/00* (2006.01)
*A61F 2/04* (2006.01)

(52) U.S. Cl. .......... 623/23.68; 604/8; 604/9; 623/23.64; 623/23.65; 623/23.67

(58) Field of Classification Search ................ 604/8–10; 623/23.64, 23.65, 23.67, 23.68; 606/108; 128/898
See application file for complete search history.

(56) References Cited

U.S. PATENT DOCUMENTS

| | | |
|---|---|---|
| 4,315,509 A | 2/1982 | Smit |
| 4,501,264 A | 2/1985 | Rockey |
| 4,592,339 A | 6/1986 | Kuzmak et al. |
| 4,763,653 A | 8/1988 | Rockey et al. |
| 5,088,979 A | 2/1992 | Filipi et al. |
| 5,188,104 A | 2/1993 | Wernicke et al. |
| 5,199,430 A | 4/1993 | Fang et al. |
| 5,226,429 A | 7/1993 | Kuzmak |
| 5,231,988 A | 8/1993 | Wernicke et al. |
| 5,246,456 A | 9/1993 | Wilkinson |
| 5,259,847 A | 11/1993 | Trambert |
| 5,263,480 A | 11/1993 | Wernicke et al. |
| 5,306,300 A | 4/1994 | Berry |
| 5,308,326 A | 5/1994 | Zimmon |
| 5,423,872 A | 6/1995 | Cigaina |
| 5,514,175 A | 5/1996 | Kim et al. |

(Continued)

FOREIGN PATENT DOCUMENTS

| | | |
|---|---|---|
| WO | WO 01/41671 A2 | 6/2001 |
| WO | WO 01/89393 A1 | 11/2001 |

(Continued)

OTHER PUBLICATIONS

Product Brochure, "Atrostim Phrenic Nerve Stimulator," AtroTech Oy, P.O. Box 28, FIN-33721 Tampere, Finland, 2 pages (Jun. 2004).

(Continued)

*Primary Examiner* — Melanie Hand
(74) *Attorney, Agent, or Firm* — Merchant & Gould, P.C.

(57) ABSTRACT

A method and apparatus are disclosed for treating obesity includes an artificial fistula created between gastrointestinal organs such as between the stomach and the colon. The method includes selecting an implant comprising a passageway having an internal lumen with an inlet end and an outlet end. The passageway is positioned passing through a first wall of first gastrointestinal organ (for example, passing through the wall of the stomach) and a second wall of a second gastrointestinal organ (for example, passing through the wall of the large intestine) with the inlet end disposed within an interior of the first gastrointestinal organ and with the outlet disposed within an interior of the second gastrointestinal organ.

23 Claims, 14 Drawing Sheets

U.S. PATENT DOCUMENTS

| | | | |
|---|---|---|---|
| 5,540,730 | A | 7/1996 | Terry et al. |
| 5,549,621 | A | 8/1996 | Bessler et al. |
| 5,836,994 | A | 11/1998 | Bourgeois |
| 5,995,872 | A | 11/1999 | Bourgeois |
| 6,067,991 | A | 5/2000 | Forsell |
| 6,097,984 | A | 8/2000 | Douglas |
| 6,104,955 | A | 8/2000 | Bourgeois |
| 6,115,635 | A | 9/2000 | Bourgeois |
| 6,210,347 | B1 | 4/2001 | Forsell |
| 6,216,039 | B1 | 4/2001 | Bourgeois |
| 6,243,607 | B1 | 6/2001 | Mintchev et al. |
| 6,302,917 | B1 | 10/2001 | Dua et al. |
| 6,327,503 | B1 | 12/2001 | Familoni |
| 6,341,236 | B1 | 1/2002 | Osorio et al. |
| 6,369,079 | B1 | 4/2002 | Rubin et al. |
| 6,449,511 | B1 | 9/2002 | Mintchev et al. |
| 6,453,907 | B1 | 9/2002 | Forsell |
| 6,454,699 | B1 | 9/2002 | Forsell |
| 6,460,543 | B1 | 10/2002 | Forsell |
| 6,461,293 | B1 | 10/2002 | Forsell |
| 6,471,635 | B1 | 10/2002 | Forsell |
| 6,475,136 | B1 | 11/2002 | Forsell |
| 6,535,764 | B2 | 3/2003 | Imran et al. |
| 6,540,789 | B1 | 4/2003 | Silverman et al. |
| 6,558,400 | B2 | 5/2003 | Deem et al. |
| 6,558,708 | B1 | 5/2003 | Lin |
| 6,571,127 | B1 | 5/2003 | Ben-Haim et al. |
| 6,572,629 | B2 | 6/2003 | Kalloo et al. |
| 6,587,719 | B1 | 7/2003 | Barrett et al. |
| 6,600,953 | B2 | 7/2003 | Flesler et al. |
| 6,609,025 | B2 | 8/2003 | Barrett et al. |
| 6,611,715 | B1 | 8/2003 | Boveja |
| 6,615,084 | B1 | 9/2003 | Cigaina |
| 6,684,105 | B2 | 1/2004 | Cohen et al. |
| 6,736,828 | B1 | 5/2004 | Adams et al. |
| 6,746,489 | B2 | 6/2004 | Dua et al. |
| 6,754,536 | B2 | 6/2004 | Swoyer et al. |
| 6,853,862 | B1 | 2/2005 | Marchal et al. |
| 6,928,320 | B2 | 8/2005 | King |
| 6,993,391 | B2 | 1/2006 | Flesler et al. |
| 7,037,344 | B2 | 5/2006 | Kagan et al. |
| 2001/0011543 | A1 | 8/2001 | Forsell |
| 2001/0037127 | A1 | 11/2001 | De Hoyos Garza |
| 2002/0022851 | A1 | 2/2002 | Kalloo et al. |
| 2002/0055757 | A1 | 5/2002 | Torre et al. |
| 2002/0165589 | A1 | 11/2002 | Imran et al. |
| 2002/0183768 | A1 | 12/2002 | Deem et al. |
| 2002/0188354 | A1 | 12/2002 | Peghini |
| 2003/0018367 | A1 | 1/2003 | DiLorenzo |
| 2003/0040804 | A1 | 2/2003 | Stack et al. |
| 2003/0040808 | A1 | 2/2003 | Stack et al. |
| 2003/0045909 | A1 | 3/2003 | Gross et al. |
| 2003/0069533 | A1 | 4/2003 | Kakutani et al. |
| 2003/0078611 | A1 | 4/2003 | Hashiba et al. |
| 2003/0158601 | A1 | 8/2003 | Silverman et al. |
| 2003/0167024 | A1 | 9/2003 | Imran et al. |
| 2003/0167025 | A1 | 9/2003 | Imran et al. |
| 2003/0171760 | A1 | 9/2003 | Gambale |
| 2003/0191476 | A1 | 10/2003 | Smit |
| 2003/0199991 | A1 | 10/2003 | Stack et al. |
| 2003/0216749 | A1 | 11/2003 | Ishikawa et al. |
| 2003/0220660 | A1 | 11/2003 | Kortenbach et al. |
| 2004/0015201 | A1 | 1/2004 | Greenstein |
| 2004/0019388 | A1 | 1/2004 | Starkebaum |
| 2004/0037865 | A1 | 2/2004 | Miller |
| 2004/0039427 | A1 | 2/2004 | Barrett et al. |
| 2004/0039452 | A1 | 2/2004 | Bessler |
| 2004/0044357 | A1 | 3/2004 | Gannoe et al. |
| 2004/0059393 | A1 | 3/2004 | Policker et al. |
| 2004/0088022 | A1 | 5/2004 | Chen |
| 2004/0089313 | A1 | 5/2004 | Utley et al. |
| 2004/0092892 | A1 | 5/2004 | Kagan et al. |
| 2004/0092974 | A1 | 5/2004 | Gannoe et al. |
| 2004/0093091 | A1 | 5/2004 | Gannoe et al. |
| 2004/0107004 | A1 | 6/2004 | Levine et al. |
| 2004/0138760 | A1 | 7/2004 | Schurr et al. |
| 2004/0167583 | A1 | 8/2004 | Knudson et al. |
| 2004/0172085 | A1 | 9/2004 | Knudson et al. |
| 2004/0172086 | A1 | 9/2004 | Knudson et al. |
| 2004/0172088 | A1 | 9/2004 | Knudson et al. |
| 2004/0172142 | A1 | 9/2004 | Stack et al. |
| 2004/0176812 | A1 | 9/2004 | Knudson et al. |
| 2004/0199087 | A1 | 10/2004 | Swain et al. |
| 2005/0033331 | A1 | 2/2005 | Burnett et al. |
| 2005/0038484 | A1 | 2/2005 | Knudson et al. |
| 2005/0055039 | A1 | 3/2005 | Burnett et al. |
| 2005/0070970 | A1 | 3/2005 | Knudson et al. |
| 2005/0070974 | A1 | 3/2005 | Knudson et al. |
| 2005/0177181 | A1 | 8/2005 | Kagan et al. |
| 2005/0228504 | A1 | 10/2005 | Demarais |
| 2005/0277957 | A1 | 12/2005 | Kuhns et al. |
| 2006/0004410 | A1 | 1/2006 | Nobis et al. |
| 2006/0015125 | A1 | 1/2006 | Swain |
| 2006/0020247 | A1 | 1/2006 | Kagan et al. |
| 2006/0036293 | A1 | 2/2006 | Whitehurst et al. |
| 2007/0265709 | A1 | 11/2007 | Rajan et al. |

FOREIGN PATENT DOCUMENTS

| | | |
|---|---|---|
| WO | WO 02/087657 A2 | 11/2002 |
| WO | WO 02/089655 A2 | 11/2002 |
| WO | WO 03/094785 | 11/2003 |
| WO | WO 2004/058102 | 7/2004 |
| WO | WO 2004/086984 A1 | 10/2004 |

OTHER PUBLICATIONS

Cennamo, A. et al., "A Rare Gastric Ulcer Complication: the Gastrocolic Fistula. A Case Report," *Chirurgia Italiana*, vol. 53, No. 6, pp. 869-872 (2001).

Fazel, A. et al., "Prophylactic Pancreatic Duct Stenting: A Panacea?," *Gastroenterology*, vol. 125, No. 4, pp. 1274-1275 (Oct. 2003).

Kilgore, K. et al., "Nerve Conduction Block Utilising High-Frequency Alternating Current," *Medical & Biological Engineering & Computing*, vol. 42, pp. 394-406 (2004).

Pitsinis, V. et al., "Gastrocolic Fistula as a Complication of Percutaneous Endoscopic Gastrostomy," *European Journal of Clinical Nutrition*, vol. 57, pp. 876-878 (2003).

Schauer, P. et al, "Surgical Management of Gastroesophageal Reflux Disease in Obese Patients," *Seminars in Laparoscopic Surgery*, vol. 8, No. 4, pp. 256-264 (Dec. 2001).

Sturm, K. et al., "Energy Intake and Appetite are Related to Antral Area in Healthy Young and Older Subjects," *Am. J. Clin. Nutr.*, vol. 80, pp. 656-667 (2004).

Tavenor, T. et al., "Gastrocolic Fistula. A Review of 15 Cases and an Update of the Literature," *J. Clin. Gastroenterol.*, vol. 16, No. 3, pp. 189-191 (1993).

Thyssen, E. et al., "Medical Treatment of Benign Gastrocolic Fistula," *Annals of Internal Medicine*, vol. 118, No. 6, pp. 433-435 (Mar. 15, 1993).

U.S. Appl. No. 10/915,716 to Burnett, filed Aug. 9, 2004.

U.S. Appl. No. 10/915,716 Final Office Action mailed Mar. 19, 2009.

Wagtmans, M. et al., "Persistent Diarrhoea in Cholecystocolic and Gastrocolic Fistula after Gastric Surgery," *Netherlands Journal of Medicine*, vol. 43, pp. 218-221 (1993).

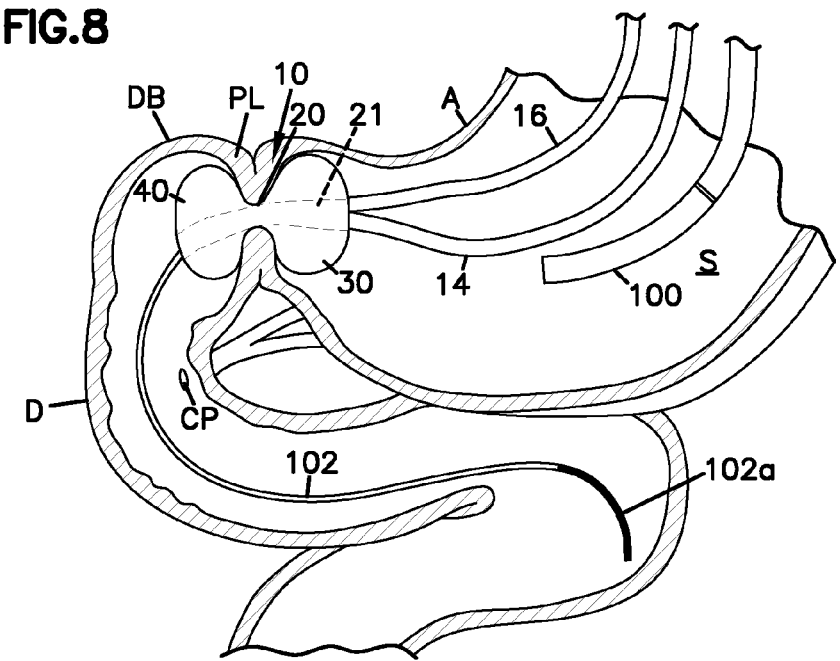
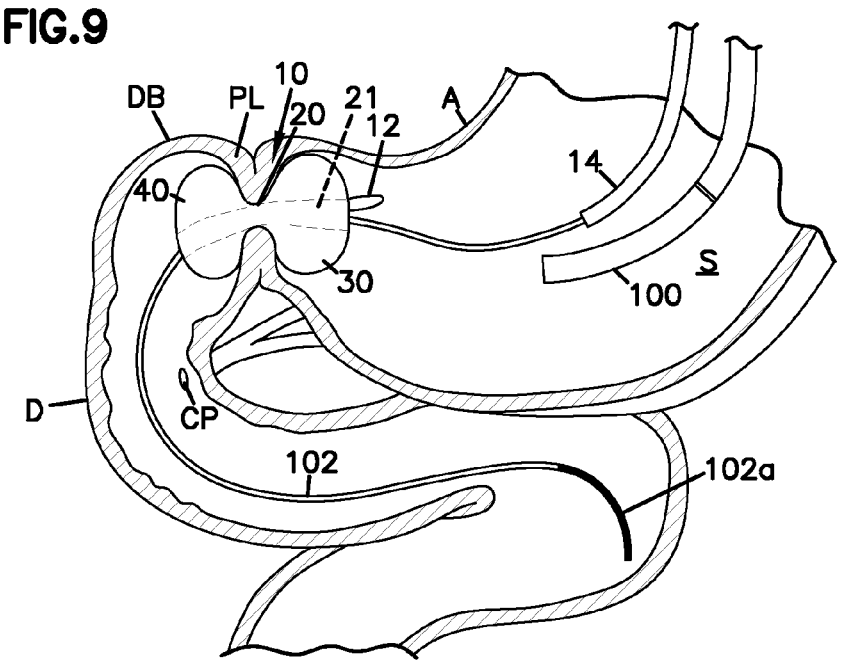

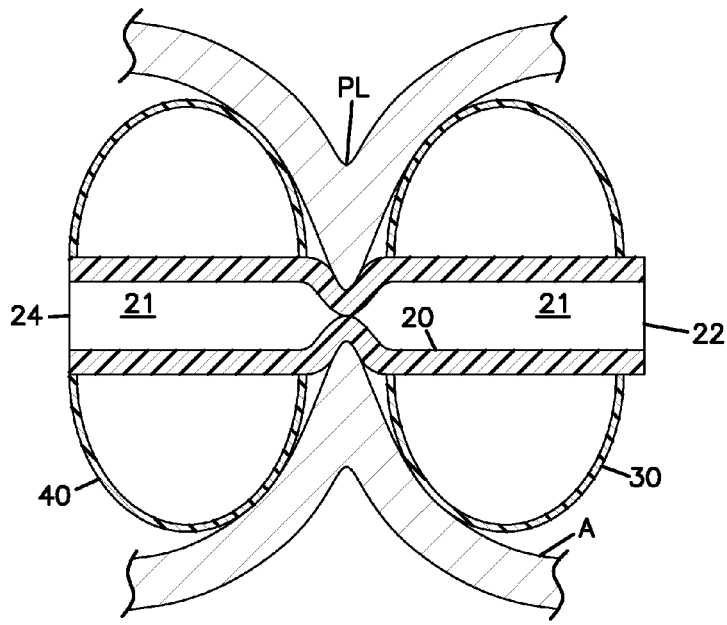
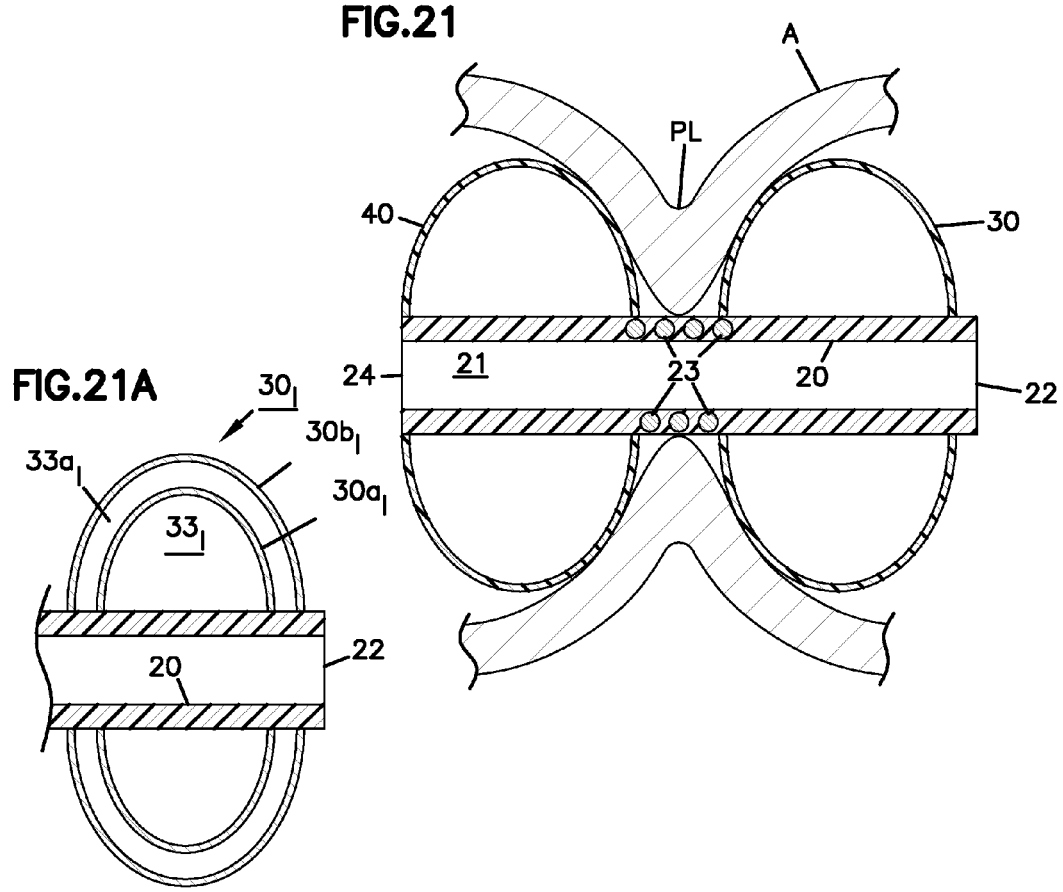

OBESITY TREATMENT AND DEVICE

I. CROSS-REFERENCE TO RELATED APPLICATION

This application is a continuation of U.S. patent application Ser. No. 11/141,869, filed May 31, 2005, now U.S. Pat. No. 7,803,195 which application is incorporated herein by reference, which claims priority to U.S. Provisional Patent Application Ser. Nos. 60/576,826; 60/589,429; 60/603,705 and 60/612,088 with respective filing dates of Jun. 3, 2004, Jul. 20, 2004, Aug. 23, 2004 and Sep. 22, 2004.

II. BACKGROUND OF THE INVENTION

1. Field of the Invention

This invention pertains to a method and apparatus for treating obesity. More particularly, this invention pertains to an apparatus and method for treating obesity with an implant in the gastrointestinal system to alter at least one of satiety, absorption and digestion.

2. Description of Prior Art

A. Obesity as a World-Wide Health Dilemma

Morbid obesity and its concurrent health risks (including diabetes, heart disease and other ailments) are of near-epidemic proportions in industrialized societies. A wide variety of treatments have been proposed and attempted to treat morbid obesity with a wide variety of efficacy and associated morbidity. These treatments include techniques to reduce stomach volume, alter gastric and intestinal motility, and alter the absorption of nutrients in the small intestine.

Clearly, obesity is a complex disease having physiologic, social and psychological components which are not fully understood. The complex nature and the enormous societal implication of obesity require a wide variety of treatment options be available to permit a physician to select a most appropriate option for a particular patient.

Even if all treatments were proven effective, no one treatment can meet the clinical needs presented by a diverse population. For example, current bariatric surgeries, such as the Roux-en-Y procedure as will be described, is not considered suitable for only so-called mildly obese patients (e.g., those with a Body Mass Index less than 35). Also, for extremely obese patients, operative risks may make this procedure undesirable.

Less invasive procedures (such as gastric banding, as will be described) have reduced surgical risk. Unfortunately, they suffer from reduced efficacy (and they are not without risks). Further, efficacy may be culturally biased. Namely, gastric banding studies show reduced efficacy in North American patients compared to European patients.

B. Selected Obesity Treatments a. Surgical Options (Non-Device)

i. Gastric Volume Reduction

Surgical approaches to gastric volume reduction include minimally invasive surgery, open surgery and endoscopic approaches to gastric volume reduction. Many such procedures have been tried and some have been abandoned due to lack of efficacy or unacceptable morbidity and mortality.

The gastric volume reduction procedures include vertical and horizontal gastroplasty in which sutures, staples or other fixation devices are used to join opposing surfaces of the stomach to create a reduced volume pouch and thereby reduce caloric intake.

Gastric stapling, as used herein, refers to staples or stitches in the stomach to reduce stomach size. These include horizontal gastroplasty and vertical gastroplasty.

Surgical gastric volume reduction is focused on reducing the fundus to induce satiety. Recent studies suggest antral volume more directly influences satiety. Strum, et al., "Energy Intake and Appetite are Related to Antral Area in Healthy Young and Older Subjects", *American Journal of Clinical Nutrition,* 80 (3), pp. 656-657 (2004).

Less invasive techniques for restricting the volume of the stomach also include a gastric partition in which the stomach wall is endoscopically cinched together to form a reduced size pouch. The cinching is performed using commercially available products such as the Bard EndoCinch™ and the Wilson-Cook Sew-Right™ cinching equipment. Such surgical equipment is generally described in U.S. Pat. No. 5,088,979 to Filipi et al. issued Feb. 18, 1992; U.S. Pat. No. 6,302,917 to Dua et al. issued Oct. 16, 2001 or PCT International Publication No. WO 01/89393 published Nov. 29, 2001.

It has been recognized that gastric volume reduction does not address all mechanisms associated with obesity. For example, patients with gastric volume reduction can defeat the effectiveness of the gastric volume reduction by modifying eating habits. For instance, a patient may graze continuously on small volume, high caloric food or may replace solid foods with high caloric liquid foods.

ii. Surgeries with Malabsorptive Components

To address deficiencies associated with gastric volume reduction, treatments have been suggested and developed for reducing the amount of nutrient absorption in the small intestine (particularly in the upper and middle portions of the small intestine—the duodenum and jejunum, respectively).

In the duodenum, ducts from the pancreas and gall bladder discharge into the small intestine through small protrusions referred to as papilla. Commonly, pancreatic exocrine secretions ("PES") flow from the pancreas in a pancreatic duct. Similarly, bile from the gall bladder flows through a bile duct. These ducts merge to form a common duct with discharges through a papilla into the duodenum. In some patients, the bile duct and pancreatic duct do not merge. They separately discharge into the duodenum at separate papilla which, usually, are in close proximity to one another.

Techniques to reduce nutrient absorption (commonly referred to as malabsorption treatments) include drug therapies for reducing lipids absorption. Such drug therapies have uncomfortable side effects, which can discourage a patient from complying with the drug therapy.

Other malabsorption treatments include surgical techniques for rerouting the intestinal system to bypass an extended portion of the small intestine. These include a so-called jejunoileal bypass. Not commonly used due to unacceptable mortality rates, a jejunoileal bypass would result in effective weight loss. Other techniques include the gastric bypass (or Roux-en Y) and duodenal switch. In both of these procedures, a large segment (e.g., in excess of 100 cm) of the small intestine (including the duodenum) are bypassed so that food content is rerouted from a small pouch formed in the upper portion of the stomach to the jejunum. As a result, the absorptive length of the small intestine is significantly shortened thereby reducing the amount of nutrients which are absorbed into the body and which support or lead to weight gain. These procedures combine the benefits of gastric volume reduction with malabsorption. Unfortunately, such surgical procedures are extremely invasive.

b. Implantable Mechanical Devices i. Gastric Volume and Delayed Gastric Emptying

1. Gastric Banding

Less invasive techniques are suggested for placing a band (referred to as LAP bands) around an upper portion of the stomach to act as a belt to reduce the size of the stomach and create a small passageway (a stoma) from a small upper pouch to the remainder of the stomach. An example of a LAP band is shown in U.S. Pat. No. 5,266,429 to Kuzmak dated Jul. 13, 1993. LAP bands and other gastric bandings are disclosed in Schauer, et al, "Surgical Management of Gastroesophageal Reflux Disease in Obese Patients", Seminars in Laparoscopic Surgery, Volume 8, Number 4, pages 256-264 (2001). Such LAP bands wrap around a portion of the fundus to create a greatly reduced volume portion of a fundus above the LAP band. Such bands create an upper chamber above the band to create a sensation of satiation after consuming only a small volume of food. See also, U.S. Pat. No. 5,549,621 to Bessler et al., dated Aug. 27, 1996; U.S. Pat. No. 5,226,429 to Kuzmak dated Jul. 13, 1993 and U.S. Pat. No. 4,592,339 to Kuzmak et al. dated Jun. 3 1986.

2. Intra-Gastric Balloons

Other techniques for reducing gastric volume size include placement of obstructions within the stomach. These include intra-gastric balloons which are filled with saline to reduce the effective volume of the stomach. Examples of such balloons or other intragastric devices include those shown in U.S. patent application publication No. US 2001/0037127 to de Hoyos Garza published Nov. 1, 2001 (describing a percutaneous intragastric balloon to treat obesity); U.S. patent application publication No. 2002/0055757 to Tone, et al., published May 9, 2002; U.S. patent application publication No. 2004/0093091 to Gannoe, et al., published May 13, 2004 (describing an anchored intragastric balloon); U.S. patent application publication No. 2004/004357 to Gannoe, et al., published Mar. 4, 2004 (describing various techniques for retaining an intragastric balloon in a location in the stomach) and U.S. patent application publication No. 2003/0158601 Silverman published Aug. 21, 2003.

3. Pyloric Narrowing

U.S. patent application publication No. 2004/0019388 to Starkebaum published Jan. 29, 2004 describes treating obesity by injecting bulking agents into the pylorus. U.S. patent application publication No. 2004/0037865 to Miller published Feb. 26, 2004 describes various techniques to narrow the pylorus to slow gastric emptying to treat obesity. For example, the '865 application describes injecting bulking or stiffening agents into the pylorus. The application also describes ablation or scarring to narrow the pylorus as well as suturing the pylorus to narrow it.

U.S. patent application publication No. 2004/0089313 to Utley, et al., May 13, 2004 describes treating the pylorus to slow or meter gastric emptying. The '313 application describes treating tissue at the pylorus with an agent to tighten tissue or with a bulking agent. The application also describes treating the pylorus with an agent to interrupt afferent nerve impulses that trigger transient sphincter relaxation. The application also describes applying ablative energy to the pylorus, using magnets to tighten the pylorus or placing bands around the pylorus.

U.S. patent application publication No. US 2002/0188354 to Peghini published Dec. 12, 2002 teaches a device to treat obesity by obstructing the gastric outlet at the pylorus. The '354 application describes a device for obstructing the pylorus to create a sensation of satiety. The obstruction is a sandglass shaped device having bulges placed on opposite sides of the pylorus (one in the stomach, the other in the small bowel) with a narrow bridge spanning the pylorus. The device is formed of plastic and endoscopically delivered and fluid filled.

U.S. patent applications Publication Nos. US 2005/0033331 and US 2005/0055039 describe pylorus obstruction devices and methods.

4. Other

There fore-going description of prior art patents is not intended to be exhaustive. In the patent literature, there are many other suggestions for treating obesity. For example, U.S. patent application Publication No. 2003/0158601 to Silverman, et al., published Aug. 21, 2003 describes injections of implants in the stomach wall near the pylorus to inhibit gastric emptying. U.S. patent application Publication No. 2004/0172142 to Stack, et al., published Sep. 2, 2004 describes covered stent-like structures in the antrum and duodenum and bridging the pylorus.

ii. Devices to Promote Malabsorption

Less invasive techniques for restricting absorption have been suggested. They include bariatric sleeve devices such as those disclosed in US Patent Application Publication Nos. 2004/0092892 to Kagan, et al., published May 13, 2004 and 2004/0107004 to Levine, et al., published Jun. 3, 2004. In these techniques, sleeves are passed through the duodenum so that chyme (the contents of the intestines) are passed through the sleeve and do not interact with the absorptive walls of the intestine. The sleeves may be perforated to permit some of the chyme material to pass through the walls of the small intestine and be absorbed as nutrients. The sleeve of the '004 application includes a stent in the pylorus. The stent keeps the pylorus permanently open to induce a so-called "dumping syndrome".

The bypass of the duodenum results in reduced absorption of desired nutrients (e.g., calcium) as well as undesirable nutrients (such as fat). Particularly, the loss of calcium absorption is significant since such loss can lead to osteoporosis.

A suggestion has been made to divert the digestive enzymes from the pancreas past the duodenum. Such a suggestion is shown in the afore-mentioned US Patent Application Publication No. 2004/0092892. In an embodiment of the '892 application, a tube is placed through the papilla and into the ducts of the gall bladder and the pancreas. A distal end of the tube is positioned significantly distal to the papilla such that pancreatic exocrine secretion and bile are diverted significantly distally to the papilla resulting in a reduction of absorption.

While pancreatic diversion is scientifically interesting, cannulation of the pancreatic duct carries significant risks. Such cannulation of the pancreatic duct has been performed in endoscopic retrograde cholangiopancreatography (ERCP). Patients under-going ERCP and/or related procedures are known to have a higher likelihood of developing pancreatitis. It has been reported that the incidence of post-ERCP pancreatitis can be as high as 28%. Fazel et al., "Prophylactic Pancreatic Duct Stenting: A Panacea", *Gastroenterology, Vol.* 124, No. 4, pp. 1274-1275 (2003). Pancreatitis is a very serious disease which can be fatal.

c. Electrical Neural Stimulation

There have been a number of suggestions to treat obesity by applying electrical stimulation. For example, two patents assigned to Cyberonics, Inc. describe purported obesity treatments involving stimulation signals applied to the vagus nerve to up-regulate vagal activity to near a so-called "retching threshold". These are U.S. Pat. Nos. 6,587,719 and 6,609,025).

U.S. Pat. No. 6,615,084 to Cigaina dated Sep. 2, 2003 (assigned to Transneuronix) delivers direct smooth muscle stimulation to the stomach through a laparoscopically placed lead connected to an implantable pulse generator. Similarly, U.S. Pat. No. 5,423,872 to Cigaina dated Jun. 13, 1995 describes placing electrodes on the abdominal wall.

A number of patents and patent applications are assigned to Intrapace Inc pertaining to an endoscopically delivered direct stimulation device for the treatment of obesity. Examples of these are U.S. Pat. No. 6,535,764; US 2003/0167025; US 2003/016024; WO 02/087657; and WO 02/089655.

Also, proposed stimulation therapies include technologies to provide direct gastric stimulation to create a 'banding' effect on the stomach formed by contracted muscle. U.S. Pat. No. 6,571,127 to Ben-Haim et al., dated May 27, 2003 describes applying a field to a GI tract to increase the force of contraction. U.S. Pat. No. 6,600,953 to Flesher et al., dated Jul. 29, 2003 describes a set of electrodes on the stomach which cause a contraction to decrease a cross-section of the stomach.

d. Electrical Neural Block

Recent novel treatments include vagal modulation to block neural impulses on the vagus nerve to down-regulate pancreatic exocrine secretion production as well as alter gastric accommodation. Such treatments are shown in U.S. Patent Application Publication No. 2004/0172086 A1 to Knudson, et al.

III. SUMMARY OF THE INVENTION

A method and apparatus are disclosed for treating obesity. In one embodiment, an artificial fistula is created between gastrointestinal organs such as between the stomach and the colon. The method includes selecting an implant comprising a passageway having an internal lumen with an inlet end and an outlet end. The passageway is positioned passing through a first wall of first gastrointestinal organ (for example, passing through the wall of the stomach) and a second wall of a second gastrointestinal organ (for example, passing through the wall of the large intestine) with the inlet end disposed within an interior of the first gastrointestinal organ and with the outlet disposed within an interior of the second gastrointestinal organ. An additional embodiment, which may be used in combination or separately, includes a passageway defining a lumen with an inlet and an outlet. The passageway is sized to be passed through a pylorus of a patient with a lumen inlet residing in a stomach of a patient and with a lumen outlet residing in a duodenum of the patient. The lumen is dimensioned to restrict a flow of contents to an amount less than a flow of stomach contents through an untreated pylorus.

IV. BRIEF DESCRIPTION OF THE DRAWINGS

FIG. 8 depicts the device of FIG. 7 after further expansion of the expandable chambers;

FIG. 9 depicts the device of FIG. 8 after removal of an expansion catheter;

FIG. 20 is a longitudinal cross-sectional view of a device with a passageway which can collapse in response to pyloric forces;

FIG. 21 is the view of FIG. 20 where the passageway is reinforced to resist collapse in response to pyloric forces;

FIG. 21A illustrates an alternative embodiment with a double walled chamber for drug delivery;

V. DESCRIPTION OF A PREFERRED EMBODIMENT

Figure 1:
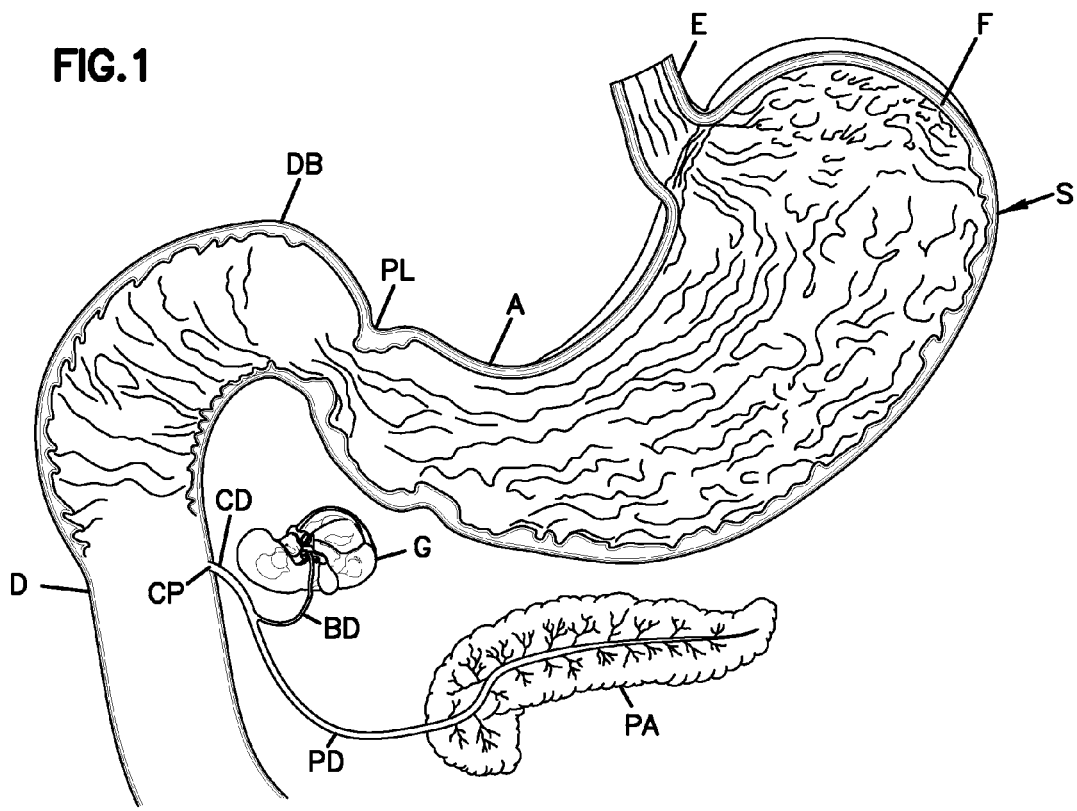
FIG. 1 is a schematic representation of a patient's gastrointestinal system illustrating various anatomic components.

In the following detailed description of some exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

A. Relevant Anatomy and Physiology

With initial reference to FIG. 1, relevant aspects of a patient's gastrointestinal system are illustrated. These include the stomach S which is provided with food from the esophagus E. A lower esophageal sphincter LES is shown positioned between the esophagus E and the stomach S. The lower esophageal sphincter normally provides control of reflux of stomach contents into the esophagus E.

On a proximal or lower end of the stomach S, the stomach discharges into the superior duodenum D which is an upper portion of the small intestine. The superior duodenum D and the stomach S are separated by a pyloric valve or sphincter PL. Normally closed, the pyloric valve PV opens to permit gastric emptying from the stomach into the duodenum D.

A pancreatic duct PD extends from the pancreas P and discharges into the superior duodenum D. Bile also passes through a separate bile duct BD. In most patients, the bile duct BD merges with the pancreatic duct PD to form a common duct CD which enters into the duodenum D at a common papilla CP. The common papilla CP is also referred to as the "ampulla of vater" or the "papilla of vater".

The upper portion of the stomach (i.e., the fundus F) receives food from the esophagus E. The lower portion of the stomach (the antrum A) is a region of greatest grinding and digestion as well as the source of compulsive forces (antropyloric waves) for urging digested food (chyme) through the pylorus PL and into the most proximal end of the duodenum D (the duodenal bulb DB).

Having described the relevant anatomy, a description of the present invention will now be provided. First to be described will be a device to treat obesity by narrowing the pylorus to delay gastric emptying. Next, a device to create an artificial gastric-colonic fistula will be described.

As will become apparent, either of the two following concepts can be separately used to treat obesity. However, last to be described will be a description of a treatment method incorporating a coordinated usage of both concepts.

B. Pyloric Narrowing and Delayed Gastric Emptying a. General Description Structure of the Pyloric Device

Figure 2:
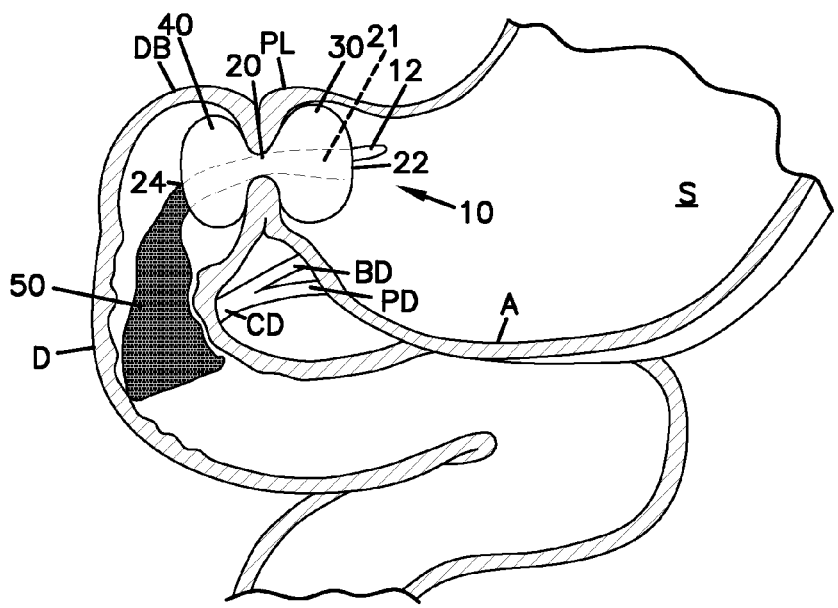
FIG. 2 depicts one exemplary embodiment of a device according to the present invention in one location within the gastrointestinal system of a patient and with the device in FIG. 2 showing an optional malabsorption sleeve.

FIG. 2 depicts a first embodiment of a device 10 according to the present invention. In FIG. 2, the device 10 is shown deployed within the gastrointestinal system of a patient. The device 10 includes a passageway 20, a first expandable chamber 30, and a second expandable chamber 40. An optional sleeve 50 is located distal of the second expandable chamber 40.

The device 10 is deployed with the passageway 20 spanning the pylorus PV. The first expandable chamber 30 of the device 10 is located within the gastric antrum A. The second expandable chamber 40 of the device 10 is located in a proximal end of the duodenum D (the "duodenal bulb") distal of the pyloric sphincter PV. As shown in FIG. 2, the device 10 may include an optional expansion port 12.

As will be described, port 12 is used to expand one or more expandable chambers (i.e., chambers 30, 40) of the device 10. The optional sleeve 50 may preferably extend into the duodenum with or without extension into the jejunum. The sleeve 50 provides a partial or full bypass of a length of absorptive tissue of the duodenum such that absorption of nutrients passing therethrough may be reduced or prevented.

The foregoing general description of the device 10 is intended to facilitate an understanding of the deployment of the device 10 as will now be described. It is intended an understanding of the deployment and positioning of the device 10 will facilitate an understanding of a further specific discussion of the construction of the device (including material selection and sizing of components with respect to anatomic features).

b. Deployment of the Pyloric Device

The device 10 has a distinct advantage over many other prior art treatments in that it can be delivered endoscopically without the need for general anesthetic. Deployment of the device 10 may be through any suitable method. By way of non-limiting example, such a deployment is illustrated in FIGS. 3-9. These Figures show insertion of the device 10 over a flexible guidewire that is placed in the small intestine during an initial esophagogastroduodenoscopy (EGD).

Figure 3:
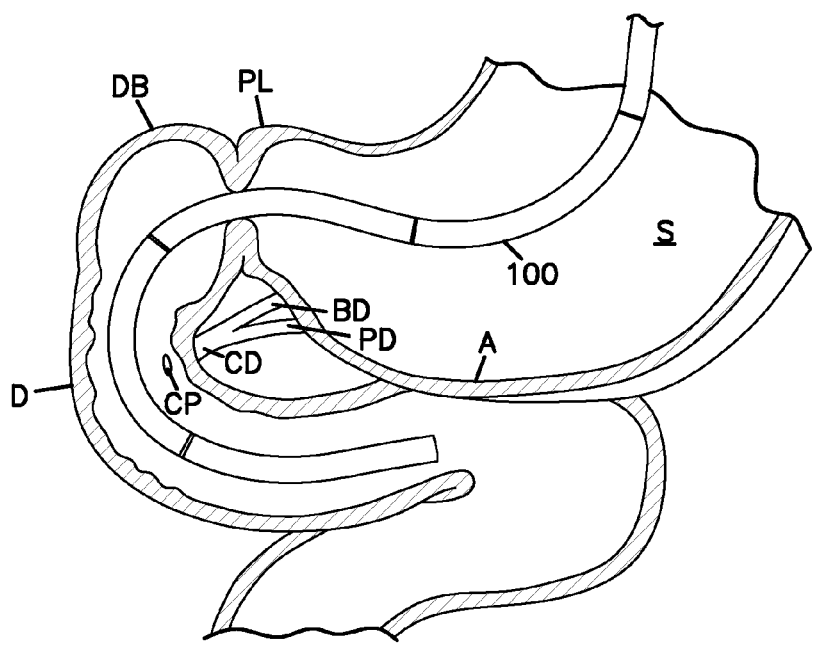
FIG. 3 depicts an esophagogastroduodenoscope advanced from the stomach into the duodenal segment of the small intestine during a deployment procedure.
Figure 4:
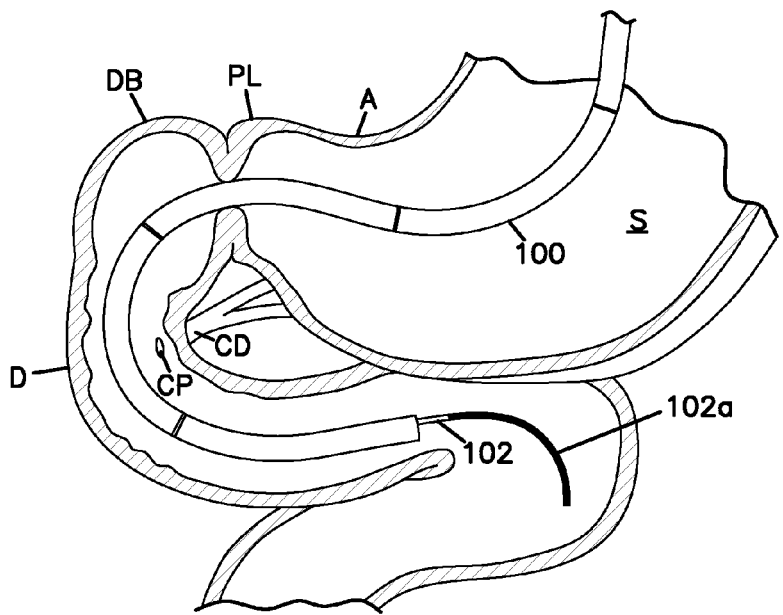
FIG. 4 depicts a guidewire extending from the esophagogastroduodenoscope.

FIG. 3 depicts positioning of a esophagogastroduodenoscope 100 within the duodenum D. The scope 100 can be placed orally, as in conventional, to pass through the esophagus E and into the stomach S and be advanced into the duodenum D.

A guidewire 102 (shown in FIG. 4) is disposed within an interior lumen of the scope 100. As shown in FIG. 3, the esophagogastroduodenoscope 100 is retracted proximally while leaving the guidewire 102 in position within the duodenum D.

Figure 5:
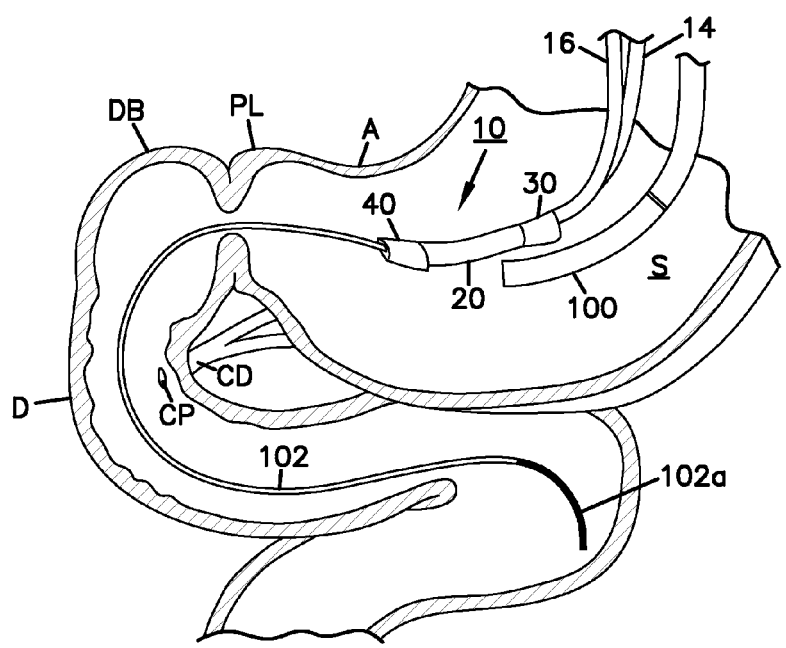
FIG. 5 depicts a device according to the present invention being advanced over the guidewire of FIG. 4.

A device 10 such as that depicted in FIG. 1 is passed over the guidewire 102 by passing the wire 102 through a lumen 21 of the hollow passageway 20 (FIG. 5). A catheter 14 is also passed over the guidewire 102 proximal to the device 10. The catheter 14 acts as a push tube to be urged against the device 10 and push it distally as shown in FIG. 5.

As shown in FIG. 5, the device 10 is shown in a collapsed state with chambers 30, 40 deflated. An inflation catheter 16 is connected to expansion port 12 to provide an expansion fluid to later inflate the chambers 30, 40 as will be described.

Also as shown in FIG. 5, the esophagogastroduodenoscope 100 is preferably reinserted into the stomach alongside the device 10 of the present invention to allow for direct visualization of the deployment of the device 10. It will be appreciated that for small sized devices 10, the device 10 may be inserted through a working channel in the esophagogastroduodenoscope 100.

Figure 6:
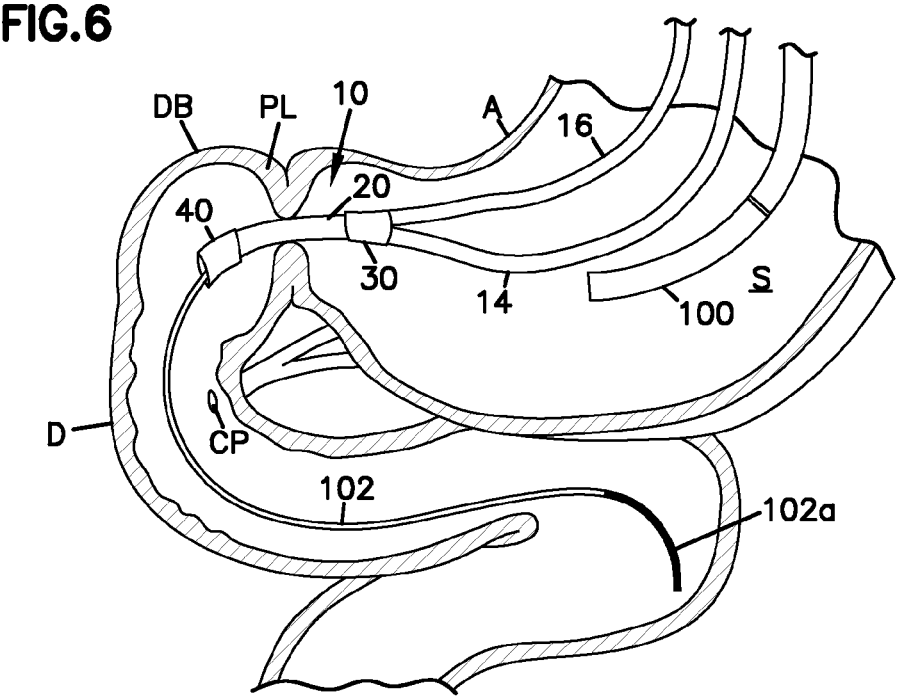
FIG. 6 depicts the device of FIG. 5 in position bridging the pylorus of the patient.

The device 10 is advanced distally over the guidewire 102 by advancing the push catheter 14 to push the device 10. Such advancement continues until the distal expansion chamber 40 of the device 10 is located within the duodenum D just distal to the pylorus PV as shown in FIG. 6. The expansion catheter 16 is advanced with the device 10.

FIG. 6 illustrates a preferred deployment position in which the distal expandable chamber 40 is located within the duodenal bulb past the pyloric sphincter PV. The proximal expandable chamber 30 is located within the gastric antrum GA. If the device 10 includes an optional sleeve 50 as depicted in FIG. 1, it may be advantageous to advance the entire device 10 to a location farther into the duodenum D followed by movement of the device 10 proximally during deployment to reduce the likelihood that the sleeve 50 is folded back upon itself within the duodenum D.

Figure 7:
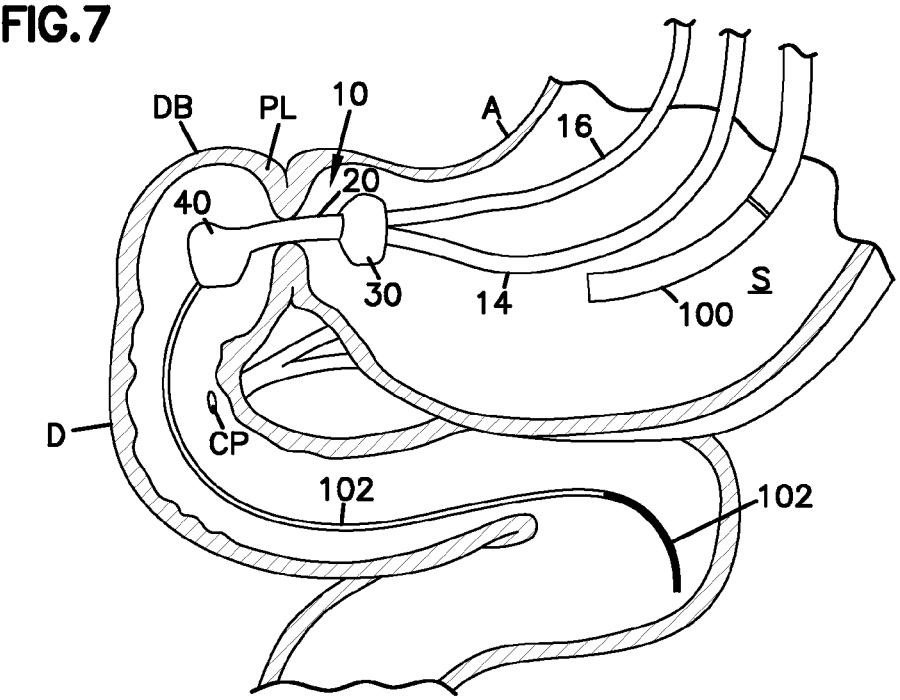
FIG. 7 depicts the device of FIG. 6 during expansion of expandable chambers.

After the device 10 is properly located within the gastrointestinal tract (as seen in, e.g., FIG. 6), the expandable chambers 30 and 40 can be expanded. Expansion of both chambers 30 and 40 is depicted in FIGS. 7 and 8.

If expansion is achieved by an attached expansion catheter 16 (as illustrated), the catheter 16 may preferably be separated from the device 10 after expansion and removed. FIG. 9 depicts the device 10 with chambers 30, 40 fully expanded and with expansion catheter 16 removed.

Withdrawal of the push catheter 14 is also illustrated in FIG. 9. In some instances, it may be advantageous to use the esophagogastroduodenoscope 100 to apply pressure in the distal direction on the device 10 to assist in removal of an expansion catheter 16 from, e.g., expansion port 12 on the device 10. Such distal pressure prevents undesired proximal displacement of the device 10 from the desired deployed position illustrated in the Figures.

Applying distal pressure with the scope 100 as described is particularly desirable where the catheter 16 is fit onto the port 12 in a sliding engagement as illustrated. Alternatively, an expansion catheter 16 may be attached to expansion port 12 using a clip or other structure that can be opened to allow removal of the expansion catheter 16. Other non-sliding contacts and removals can include severing of the connection between the catheter 16 and port 12.

After the catheters 14 and 16 are removed, the guidewire 102 is distally withdrawn. Removal of the guidewire 102 leaves the expanded device 10 in position as seen in FIG. 2.

c. Removal of the Pyloric Device

One of the many benefits of the treatment of the present invention is that it is reversible by removing the device 10. Removal of a device 10 may be effected by a variety of methods.

Removal will typically involve deflation or another action that causes the expanded chambers 30 and 40 to have a reduced volume. If the expandable chambers 30 and 40 are expanded using a fluid, puncturing the chambers 30 and 40 may be used to deflate them.

If the chambers are in fluid communication with each other, puncturing one of the chambers may be sufficient to deflate both chambers. If the chambers are independently expandable as described herein, each of the chambers may need to be deflated separately.

It may be desirable to deflate the distal chamber 40 first to prevent distal migration of the device that could occur if the proximal chamber 30 was deflated first.

If puncturing is to be used to deflate the chambers, the puncturing may be accomplished using, e.g., biopsy forceps, needle, a snare with or without a short delivery of cauterizing energy, endoscopic scissors, etc. It may also be advantageous to use a snare in combination with a needle or other puncturing device such that the device of the present invention can be grasped or secured for removal after deflation. Grasping the device with a snare or other device before deflation may help prevent distal migration during the removal process.

The devices of the present invention may preferably be adapted for delivery into the gastrointestinal system endoscopically, although other placement techniques and methods may also be possible. A variety of different delivery methods and structures may be described in, e.g., U.S. Pat. Nos. 4,315,509 (Smit); 4,501,264 (Rockey); and 5,306,300 (Berry); as well as U.S. Patent Publication No. US 2003/0040804 A1 (Stack et al.).

d. Additional Description of Device Structure

Figure 10:
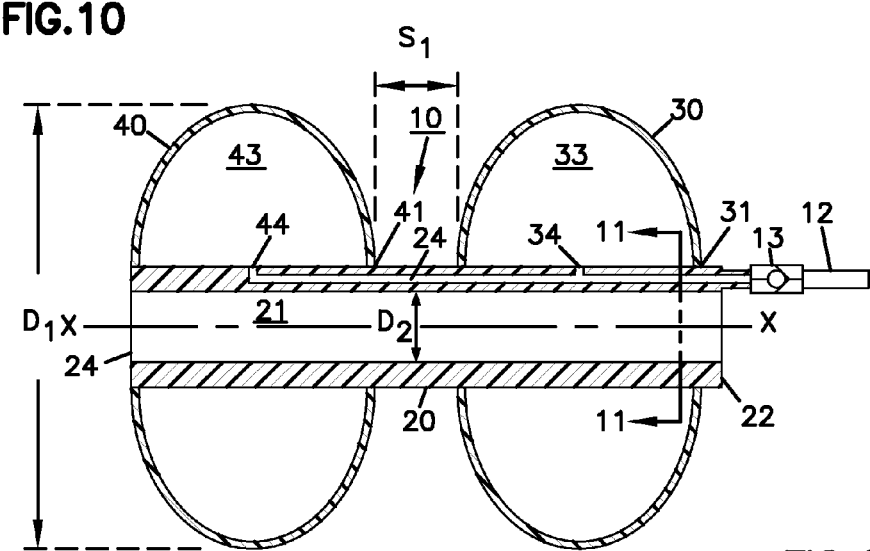
FIG. 10 is a longitudinal cross-sectional view of the device of FIG. 2 without showing an optional sleeve.
Figure 11:
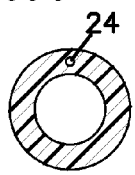
FIG. 11 is a view taken along line 11-11 of FIG. 10.

FIGS. 10 and 11 depicts the device of FIG. 2 outside of the gastrointestinal system of the patient. In FIG. 10, the optional sleeve 50 is not shown.

The passageway 20 is a hollow, flexible tube having an internal lumen 21 with an inlet 22 and an exit 24 spaced apart along a longitudinal axis X-X. As deployed within the gastrointestinal system of a patient as depicted in FIG. 2, it is preferred that the inlet 22 be located within the stomach (preferably within the gastric antrum) and that the outlet 24 be located distal of the pyloric sphincter PL, preferably within the duodenal bulb BD. Preferably, the passageway 20 is bendable transverse to the axis X-X to permit ease of deployment as well as ease of passing the device 10 in the event it becomes displaced.

The device 10 includes the first expandable chamber 30 located proximate the inlet 22 of the passageway 20. The expandable chamber 30 may preferably be generally toroidal in shape with an axial opening 31 through which the passageway 20 is positioned. By "generally toroidal" it is meant that the expandable chamber 30 may take the shape of a toroid in general. The shape may, however, not necessarily be a geometrically perfect toroid. Rather, the toroid may not exhibit symmetry in any plane.

The device 10 also includes a second expandable chamber 40 located proximate the outlet 24 of the passageway 20. The second expandable chamber 40 may also preferably be generally toroidal in shape as discussed above in connection with the first expandable chamber 30. The expandable chamber 40 has an axial opening 41 through which the passageway 20 is passed. Central positioning of the outlet 24 in the chamber 40 maximizes the displacement of the outlet 24 from the walls of the duodenum thereby reducing a risk of bile reflux into the stomach.

The expansion chambers 30, 40 are bonded to the passageway 20 in any suitable means. For example, they can be bonded to the passageway in the same manner inflatable balloons are bonded to balloon-tipped catheters. The chambers 30, 40 define internal bounded volumes 33, 43 for receiving an inflating medium as will be described.

The tubular wall of the passageway 20 contains an inflation lumen 24 in fluid flow connection with volumes 33, 43 via ports 34, 44. The inflation port 12 is connected to the inflation lumen 12 by a check-valve 13 (schematically illustrated).

The first and second expandable chambers 30 and 40 be separated along the longitudinal axis X-X of the passageway 20 by a spacing $S_1$. The spacing $S_1$ is selected to locate the proximal expandable chamber 30 within the gastric antrum opposing the pylorus PL while the distal expandable chamber 40 is located in the duodenal bulb B opposing the pylorus PL. A representative spacing $S_1$ is about 5 to 10 mm but may include inflation so chambers 30, 40 are snug against opposing tissue with a force less than a force that would otherwise result in pressure necrosis. With this spacing $S_1$, the chambers provide a squeeze against the pylorus PL to prevent migration of the device 10.

The diameter $D_1$ of the expansion chambers 30, 40 is also selected to prevent migration of the device 10 after placement. Preferably, this diameter $D_1$ is greater than the maximum opening of the pylorus PL. By way of non-limiting example, the pylorus of an adult may open sufficiently large to pass an object of 2.5-3 cm. Therefore, the chamber diameter $D_1$ is preferably greater than 4 cm and more preferably greater than 5 cm. The surface of the proximal chamber 30 opposing the pylorus P may be reinforced to stiffen the chamber 30 to further resist migration.

Also, the chamber diameter $D_1$ is selected to avoid undue pressure against opposing tissue. Excessive pressure against tissue can lead to pressure necrosis, ulceration or other injury. The duodenum D has a thinner wall than the antrum A and is more susceptible to pressure injury. During inflation of the chambers 30, 40, pressure can be monitored to avoid undue pressure.

The internal diameter $D_2$ of the lumen 21 is selected to be narrower than a maximum opening of the pylorus PL. In a presently preferred embodiment, the size of the lumen 21 is selected to have a maximum diameter of about 8 mm. As a consequence, a smaller amount of digested food can be passed into the duodenum for any given amount of time. In addition to limiting the amount of chyme available for absorption, the invention results in delayed gastric emptying (increased gastric retention) with an increased sense of satiety. Preferably, the wall of the passageway 20 is reinforced so that the lumen 21 remains patent in response to opposing forces of the pylorus which would otherwise urge the lumen 21 to close.

e. Alternative Structures i. Separately Inflatable Chambers

Figure 12:
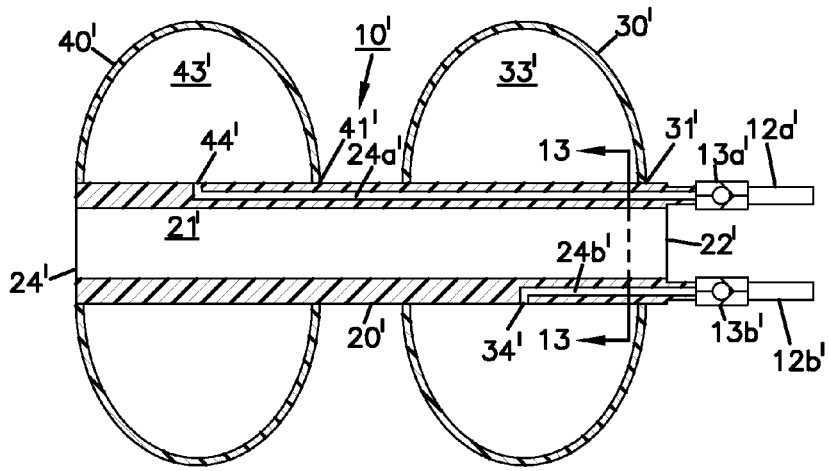
FIG. 12 is a longitudinal cross-sectional view of an alternative embodiment of the device of the present invention.
Figure 13:
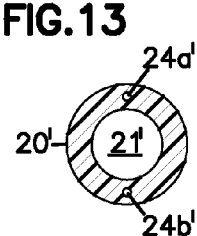
FIG. 13 is view taken along line 13-13 of FIG. 12.

FIGS. 12-13 illustrate an alternative embodiment device 10'. In the embodiment of FIGS. 12-13, elements in common with device 10 are similarly numbered with the addition of an apostrophe to distinguish the embodiments.

In the device 10', the chambers 30', 40' are separately inflatable. Instead of having a common inflation lumen 24 of device 10, device 10' has two inflation lumens 24a', 24b' separately connected to chambers 40', 30' through ports 44', 34'. Each lumen 24a', 24b' has a separate inflation port 12a', 12b' and check valve 13a', 13b'.

With this embodiment, greater pressure can be applied to the proximal chamber 30' to increase antral pressure and create an enhanced sensation of satiety. The increased pressure of proximal chamber 30' is not transmitted to the distal chamber 40' and, hence, not transmitted to the duodenal wall.

ii. Adjustable Passageway Lumen

In the preferred embodiment, the lumen 21 remains patent at all times and at a constant diameter $D_1$ (FIG. 10). If desired (and as illustrated in FIG. 21), the passageway 20 can include reinforcing rings 23 of stainless steel or other reinforcing structure to resist collapse of the lumen 21 in response to pyloric forces. Alternatively, the passageway 20 can be selected of materials for the lumen to be collapsible to close in response to pyloric forces as illustrated in FIG. 20. In such case, the lumen diameter is not constant but varies between closed and the maximum diameter $D_1$ representing a maximum lumen opening.

Figure 14:
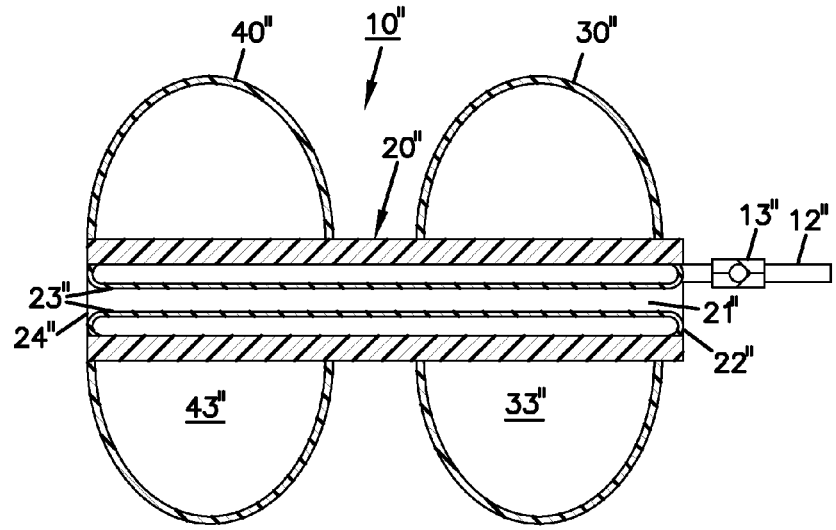
FIG. 14 is a longitudinal cross-sectional view of a further alternative embodiment of the device of the present invention.
Figure 15:
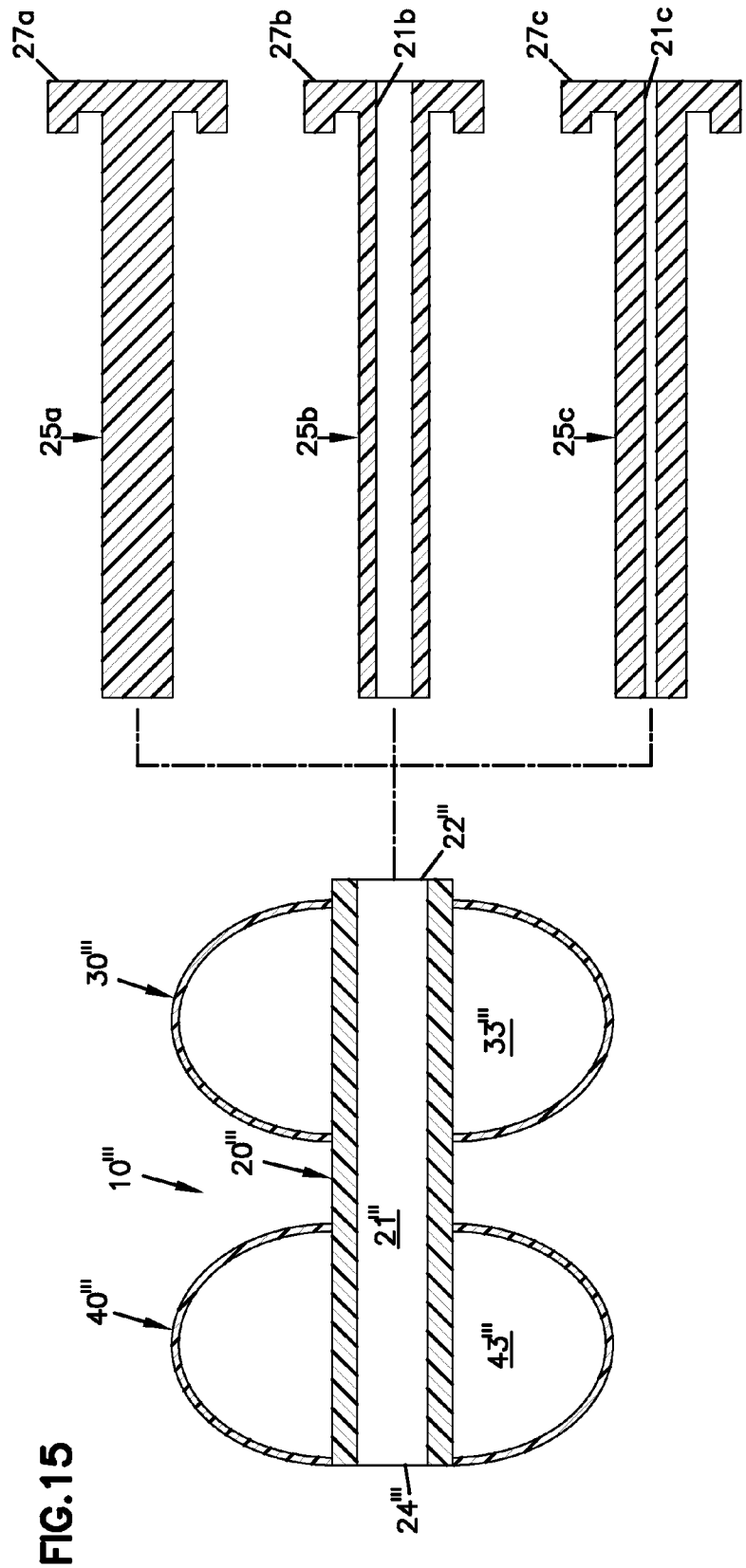
FIG. 15 is a longitudinal cross-sectional view similar to that of FIG. 10 (without showing an inflation lumen) and showing, in exploded format, optional plug inserts.

FIGS. 14 and 15 illustrate alternative embodiment devices 10" and 10"'. In the embodiment of these figures, elements in common with device 10 are similarly numbered with the addition of double and triple apostrophes to distinguish the embodiments. For ease of illustration the inflation lumens (such as lumens 24, 24a', 24b' of embodiments 10, 10') are not shown. With such plugs, a very restrictive plug can by used to promote rapid weight loss. Then, a less restrictive plug could be used to maintain a desired weight.

The device 10" of FIG. 14 has a balloon lining 23" along the length of the passageway 20" and within the lumen 21". The balloon 23" has an inflation port 12" and check valve 13". Inflation of the balloon 23" narrows the diameter of the lumen 21".

Other options are available for narrowing the passageway lumen. FIG. 15 illustrates an embodiment were plugs 25a, 25b, 25c can be placed in the lumen 21"'. The plugs 25b, 25c have a lumens 21b, 21c of progressively smaller diameter than the passageway lumen 21"'. Different plugs of different lumen sizes can be available to permit a physician to titrate a treatment for an individual patient. Indeed, a solid plug 25a could be used on a temporary basis if desired. Each plug 25a, 25b, 25c has a capped end 27a, 27b, 27c shaped to be received on end 22"' to hold the plug 25a, 25b, 25c in the lumen 21".

iii. Enlarged Antral Chambers

Figure 17:
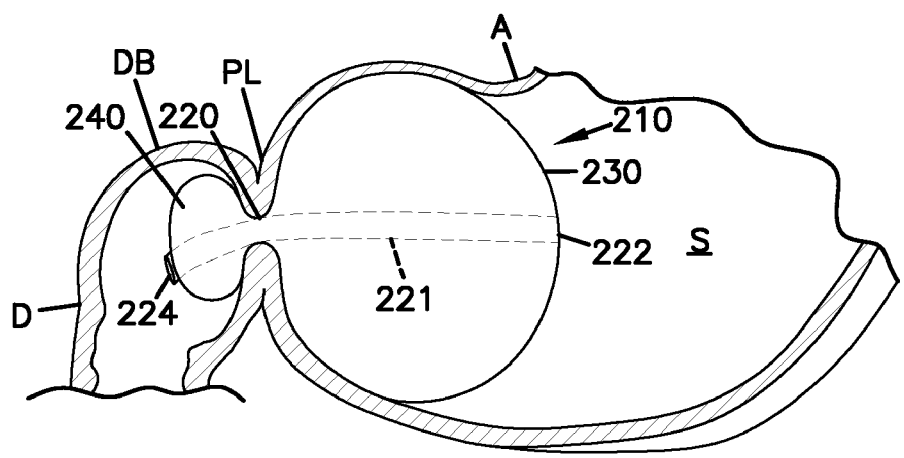
FIG. 17 is a view of a still further embodiment of the present invention in situ with a proximal expansion chamber substantially filling an antrum.

FIG. 17 illustrates an embodiment of a device 210 having a proximal expansion chamber 230, distal expansion chamber 240 and passageway 220 and lumen 221 similar to that of device 10. However, the proximal expansion chamber 230 is sized to occupy a substantial volume of the antrum A. For example, the chamber can have a maximum diameter of about 20 and length L of about 20 cm.

When inflated, the chamber 230 fills the antrum. In addition to narrowing the pylorus as in the embodiment of device 10, the device 210 (by reason of the large chamber 230) isolates stomach content from the grinding and propelling action of the antrum A thereby further enhancing the maldigestive nature of the invention. Filling chamber 230 with a compressible fluid further isolates food in the stomach S from antral grinding since the compression fluid absorbs the forces. The enlarged chamber 230 also reduces the stomach volume and has a potential for creating a bigger satiety effect.

Figure 18:
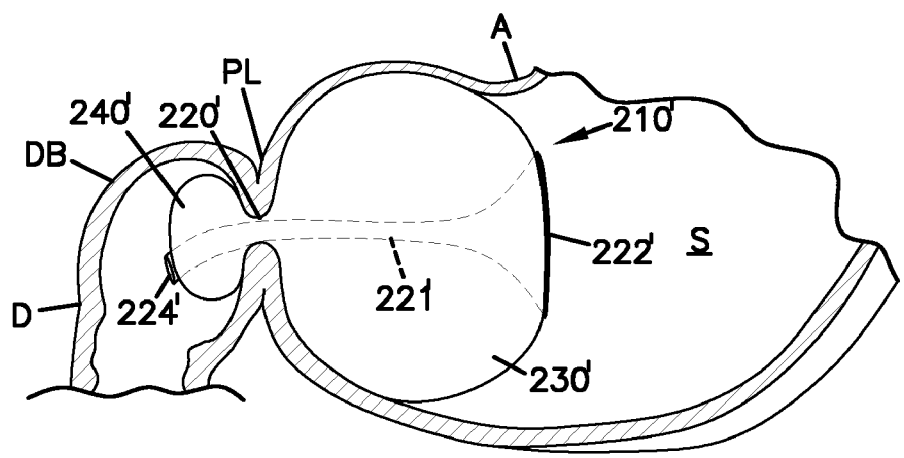
FIG. 18 is a view similar to that of FIG. 17 and showing a modified version of the device of FIG. 17.

In FIG. 17, the lumen 221 is of uniform cross-section throughout. FIG. 18 illustrates an alternative embodiment. In the embodiment of FIGS. 12-13, elements in common with device 210 are similarly numbered with the addition of an apostrophe to distinguish the embodiments. In FIG. 18, the lumen 221' has an enlarged or trumpet shaped entrance end 222' of the lumen 221'. If desired, end 222' can be provided with a purse-string suture (not shown) or other mechanism to collapse end 222' for delivery or removal.

iv. Washed Inlet

Figure 23:
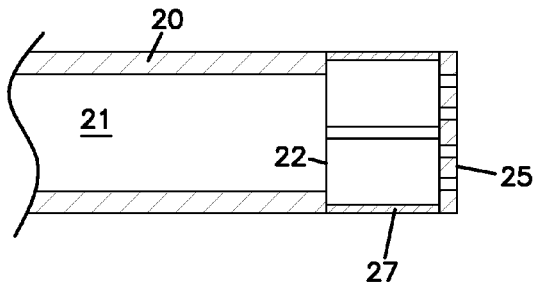
FIG. 23 is a longitudinal cross-sectional view of an inlet end of a passageway with an optional screen.

FIG. 23 illustrates a passageway inlet 22 with an optional ring 25 spaced from the inlet by support posts 27. In the event food might cover and block the ring, chyme flow between the posts 27 acts to wash the ring and clear it of debris.

v. Valved Device

Figure 19:
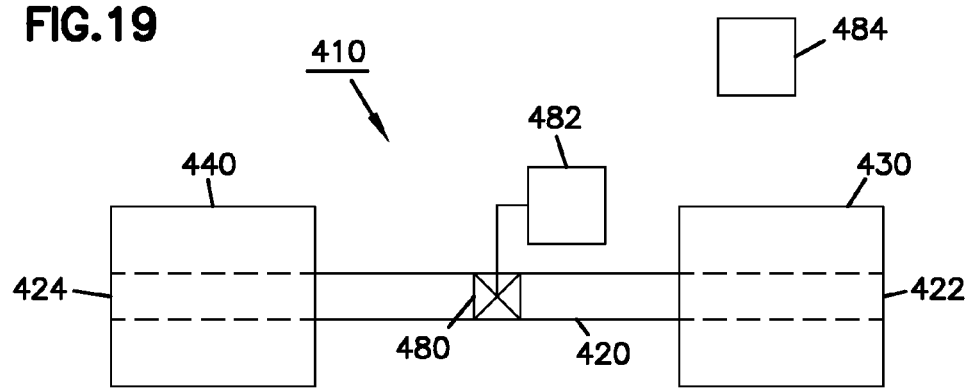
FIG. 19 is a schematic diagram of an alternative embodiment of the present invention having a valve to control flow of contents through the device.

FIG. 19 is a schematic diagram of another exemplary embodiment of the present invention. In FIG. 19, the device 410 includes a passageway 420 and proximal and distal expandable chamber 430 and 440 as described with reference to device 10.

FIG. 19 illustrates an additional optional feature as a valve 480 to control the movement of nutrients through the passageway 420. The valve 480 may have many different constructions. In some embodiments, valve 480 may be a one-way valve to reduce the likelihood that materials will move from the outlet 424 to the inlet 422 of the passageway 220, e.g., from the duodenal bulb to the stomach.

In other embodiments, the valve 480 may act as a flow restrictor by providing a reduced opening through which nutrients pass when moving through the passageway.

The size of the orifice provided by the valve 480 may be selected before the device is deployed within a patient. When employed as a static flow restrictor, the valve 480 will preferably not completely obstruct the passageway 420.

In still other embodiments, the valve 480 may be adjustable after deployment within a patient using, e.g., a control mechanism 482. The valve 480 and control mechanism 282 may be capable of completely closing the valve 480. Such closure prevents movement of nutrients through the passageway 420. Alternatively, the valve 480 and control mechanism 482 may be limited to adjusting the amount of flow restriction in the passageway 420 without the ability to completely close the passageway 420.

It may be preferred that the control mechanism 482 be controlled by a controller 484 located outside of the patient. Communication between the controller 484 and the control mechanism 482 may be accomplished by using any suitable remote control technique, e.g., telemetry, optical energy, acoustic energy, etc.

The valve 480 and control mechanism 482 (if provided) may be of any suitable construction and use any suitable actuation principles, e.g., hydraulic, pneumatic, mechanical (e.g., a shutter valve, band restriction around a passageway), magnetic, etc. Examples of some potentially suitable valve constructions may be described in, e.g., U.S. Pat. Nos. 6,067, 991; 6,210,347 B1; 6,453,907 B1; 6,454,699 B1; 6,460,543 B1; 6,461,293 B1; 6,471,635 B1; and 6,475,136 B1 (all to Forsell). At least some of the documents identified above also describe some potentially suitable controllers 284 and control techniques for use in connection with implanted valves and valve control mechanisms.

In some embodiments, the valve 480 may be controlled based on pressure. For example, the valve 480 may be controlled based on a separate pressure sensor implanted at a suitable location within the patient. Pressure control may be used as a primary control technique for opening, closing and/or adjusting the orifice in the valve 480 and/or as a safety feature wherein the valve 480 opens in response to pressures that are deemed excessive. Potentially suitable pressure control systems and techniques may also be described in at least some of the documents identified herein.

Also, although described separately, devices according to the present invention may include valves that are both one-way valves and that are configured to restrict flow, i.e., the same valve may function to prevent backflow through the passageway and restrict flow in the desired in direction. Alternatively, devices according to the present invention may include more than one valve, e.g., a one-way valve to prevent backflow and one or more additional valves to control the rate of flow through the passageway in the desired direction.

vi. Combination with Pancreatic Secretion Bypass

Figure 22:
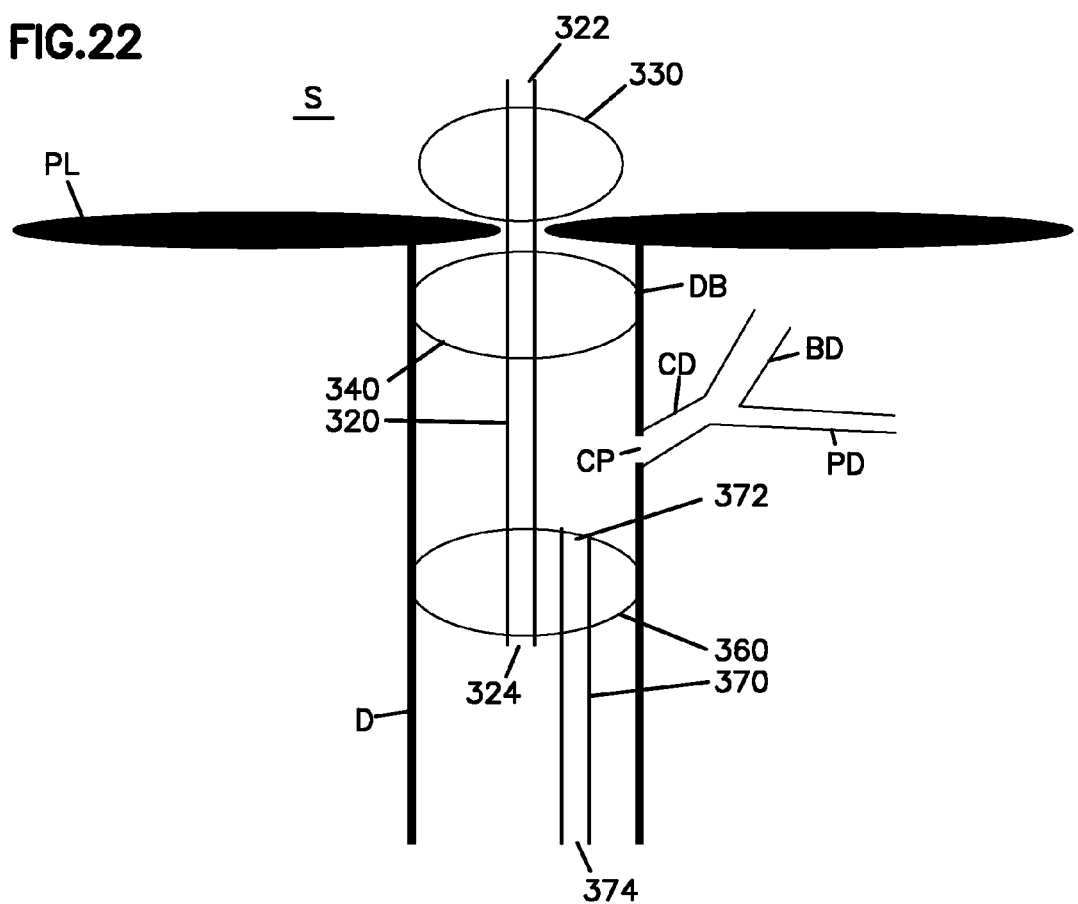
FIG. 22 is a schematic view of an apparatus and method for bypassing a length of absorptive tissue of the duodenum.

Still another embodiment of the present invention is schematically depicted in FIG. 22. The depicted device 310 includes a first expandable chamber 330 and a second expandable chamber 340 which can be as previously described. The first expandable chamber 330 is preferably located on the antral side of the pyloric sphincter (i.e., proximal the pyloric sphincter) and the second expandable chamber 340 is preferably located on the opposite side of the pyloric sphincter PL.

The depicted device further includes a passageway 320 as described with reference to device 10 but longer for reasons that will become apparent. The passageway has inlet 322 that is preferably located within the stomach S (preferably within the gastric antrum A) and an exit 324. Unlike the other embodiments described herein, the passageway 320 extends to a third expandable chamber 360 such that the exit 324 of the passageway 320 is located distal of the chamber 360. As a result, food entering the passageway 320 through the inlet 322 preferably does not exit the passageway 320 until it passes the third expandable chamber 360. When deployed, it is preferred that the third expandable chamber 360 be located distal to the common papilla CP and be sized such that when expanded, the chamber 360 contacts the wall of the small intestine such that fluid cannot pass between the chamber 360 and the interior of the small intestine.

The common papilla CP is the exit point for the common duct CD which carries secretions from the pancreas (enzymes and proteases) and bile acids from the liver via the gall bladder. The expandable chamber 360 preferably contains a tube 370 to collect the majority of bile and pancreatic secretions and channel these secretions further down the small intestine (e.g., to the jejunum) to delay or prevent the bile and pancreatic secretions from interacting with food. It may be preferred, e.g., that the third expandable chamber 360 be located approximately 5-6 centimeters distal to the second expandable chamber 340 which should place the third expandable chamber 360 below the common papilla CP.

The tube 370 that is separate from the passageway 320 through which food passes. While the proximal surface of the chamber 360 is shown as convex, it may be concave or take some other shape such that bile and pancreatic exocrine secretions are directed into the inlet 372 of the bile channel 370. The bile channel 370 preferably transports secretions farther down the small intestine where they pass out of the tube 370 through the exit 374. Isolating the secretions in this manner delays or prevents them from interacting with food, which may thereby reduce fat/calorie absorption. The tube 370 may preferably have a length of, e.g., 150-200 centimeters.

The devices of the present invention may preferably be adapted for delivery into the gastrointestinal system endoscopically, although other placement techniques and methods may also be possible. A variety of different delivery methods and structures may be described in, e.g., U.S. Pat. Nos. 4,315, 509 (Smit); 4,501,264 (Rockey); and 5,306,300 (Berry); as well as U.S. Patent Publication No. US 2003/0040804 A1 (Stack et al.).

vii. Material Selection Options

In a preferred embodiment, the lumen 21 is described as being continuously patent. However, as an alternative embodiment, the material of the passageway 20 can be selected to that the lumen 21 may collapse in a radial direction in response to pyloric forces. In such an embodiment, the passageway 20 acts to limit the maximum opening.

The devices of the present invention may be manufactured of a variety of materials. Preferably, the materials used in the devices will be compatible with long-term exposure to ingested food, gastrointestinal fluids (e.g., low pH stomach fluids and high pH intestinal fluids), mechanical stresses associated with the gastrointestinal system, etc.

Examples of some suitable materials for the passageway, expandable chambers, sleeves, etc. may include, but are not limited to, polymeric materials (e.g., silicone elastomers, polyethylenes, polyether polyurethanes (e.g., TEGADERM), polytetrafluoroethylenes (PTFE), and other materials. One or both of the chambers (e.g., 30, 40) or other balloons (e.g., balloon 23") may be made of distensible or non-distensible material (such options being known for balloons of balloon tipped catheters).

If metallic materials such as wires, struts, meshes, etc. are incorporated into the devices of the present invention, they may include, e.g., shape memory metals (such as nickel-titanium alloys), stainless steel, etc. In some instances, the devices of the present invention may include shape memory polymers for one or more different components such as the expandable chambers, etc.

viii. Expansion Options

The preferred embodiment describes fluid to chambers 30, 40 to cause chamber expansion. The expansion port 12 may take a variety of forms dependent on the nature of the expandable chambers and the devices used to expand the chambers. For example, the expandable chambers may be expanded using fluids (liquids and/or gases) such as, e.g., saline, carbon dioxide, air, etc. In some instances, the fluids used may be selected for their viscosity characteristics.

If desired, a dye (such as methylene blue or another biologically inert but detectable material) can be added to the expansion fluid. In the event an expansion chamber is ruptured, the present of the dye in stool provides a visual indication of rupture.

It may be advantageous to incorporate features into the device to allow for visualization of the location of the device (e.g., radiopaque markers, etc.) when the device is deployed within the body of a patient. Visualization may be helpful if migration of the device is suspected after deployment. In addition, it may be helpful to manufacture the devices of the present invention of materials that have a pliability and flexibility to pass through the gastrointestinal tract if migration occurs.

A dense fluid can be used to expand the chambers 30, 40. A dense fluid adds weight to the device 10 which increases the sensation of satiety.

Other than the check valves, other options may be used to inflate the chambers. For example, the passageway material can be a self-sealing polymer. Inflation fluid can be admitted to the inflation lumen through needle injection.

Although the expandable chambers 30, 40 are described herein as expanding due to the delivery of fluids, expansion of the expandable chambers of some devices according to the present invention may be assisted by wires or other structural members made of stainless steel, shape memory metals, shape memory polymers, etc.

ix. Malabsorption Sleeve

Figure 16:
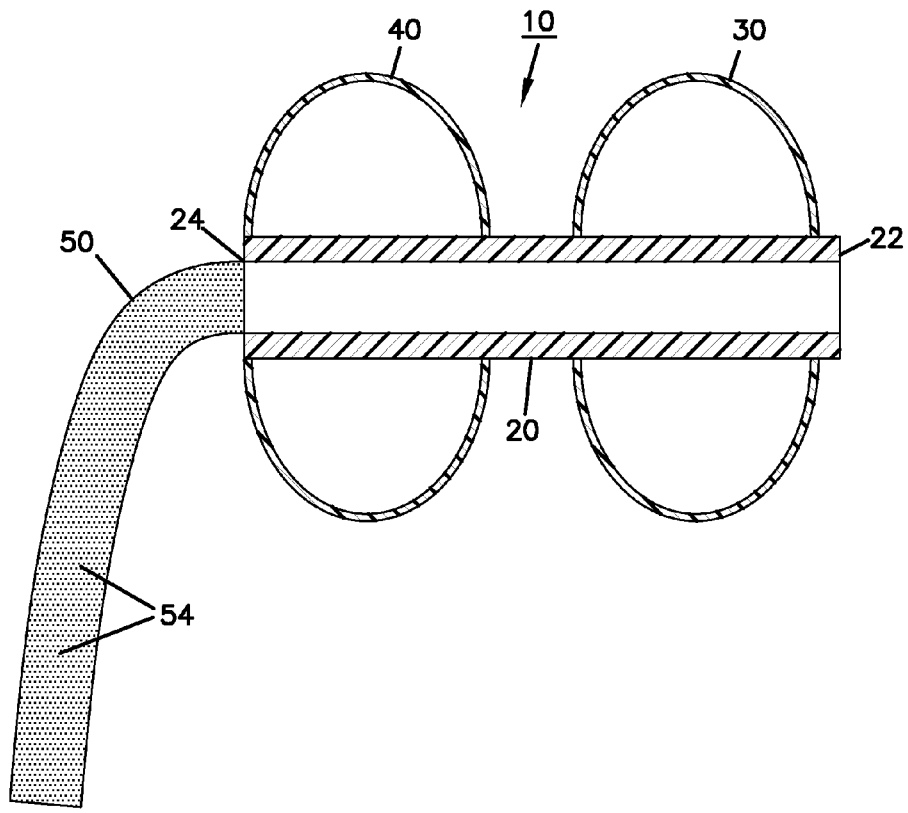
FIG. 16 is a longitudinal cross-sectional view similar to that of FIG. 10 (without showing an inflation lumen) and showing an optional sleeve.

FIGS. 2 and 16 illustrate a device 10 with an optional malabsorption sleeve 50. Nutrients exiting the outlet 24 of the passageway 20 move into the sleeve 50 before exiting the sleeve 50 at the distal end 52 of the sleeve. When the device is deployed within the gastrointestinal system of a patient such as is depicted in FIG. 1, the sleeve 50 may preferably be located within the duodenum. The sleeve 50 may have a length selected to line a predetermined length of the small bowel. Preferably, the sleeve will extend beyond the common papilla CP.

The sleeve 50 is preferably constructed such that the nutrients passing therethrough do not pass through the wall of the sleeve 50. Alternatively, the sleeve 50 may be permeable (indicated by perforations 54) for nutrients to pass through the wall of the sleeve 50 at a reduced rate. Control over nutrient permeability may be obtained by selection of the materials used for the sleeve 50, e.g., by selecting materials that are themselves permeable to the nutrients. It may also be preferred that the sleeve 50 exhibit some permeability to duodenal fluids that may, e.g., improve the motility of ingested food, reduce the likelihood of obstruction in the sleeve 50, etc.

Alternatively, the sleeve 50 could be constructed of materials that are impermeable to nutrients with permeability of the sleeve 50 being provided by structural features in the sleeve 50 such as fenestrations 54 formed in the sleeve 50.

The size, shape, spacing, etc. of the fenestrations 54 (as well as the length of the sleeve 50) can all be selected to control the absorption of nutrients within the portion of the proximal bowel occupied by the sleeve 50.

x. Drug Delivery

The residence of any of the foregoing devices (e.g., device 10) in the gastrointestinal tract provides an opportunity for convenient drug delivery. For example, the device 10 may be coated with drugs to be released over time. Also, any of the chambers (such as chambers 30, 40) may be filled with a drug solution. The material of the chambers 30, 40 may be selected to be permeable to such drugs so that they are discharged over time. The chambers 30, 40 can be re-filled as desired with a fresh supply of a drug solution.

FIG. 21A illustrates an embodiment to avoid excessive shrinkage of a chamber 30, 40 as a drug passes through a permeable chamber membrane. In FIG. 21A, a proximal chamber 30₁ is illustrated. It will be appreciated this feature may also be applied to a distal chamber (e.g., chamber 40).

In FIG. 21, the chamber 30₁ is formed of a double walled construction. The inner wall $30a_1$ is a non-permeable wall to retain fluid in the interior $33_1$ and maintain the inflation of the chamber $30_1$ to a size sufficient to resist passage through the pylorus. The inflating fluid may be any of those previously described.

An outer wall $30b_1$ surrounds the inner wall $30a_1$ with opposing surfaces defining an outer volume $33a_1$. The outer volume $33a_1$ may be filled with a drug-containing solution using separate fill ports such as those described with reference to port 12.

The outer wall $30b_1$ is selected of a material which is permeable to the drug. Accordingly, the drug is dispersed over time for the desired therapeutic effect. The outer volume $33a_1$ may be re-filled with the drug solution as needed.

The potential drugs for use with the device are many and varied. For example, such drugs could include satiety-inducing drugs such as PYY or ghrelin. Such drugs may also include enzyme inhibitors (e.g., drugs to inhibit amylase, trypsin or lipase).

C. Colonic Bypass a. General Description

FIGS. 24-27 illustrate the use of the device 10 of the foregoing description in combination with a secondary device 510 for creating an artificial fistula from the stomach S to the colon C. While the secondary device 110 can be used separately as an independent therapy, it is most preferably used in combination with a pyloric restriction device such as (but not limited to) any of the fore-going devices (e.g., device 10).

The methods, kits and systems of the present invention preferably provide for control over the flow of nutrients ingested by a subject through the normal or primary path that includes the stomach-duodenum-jejunum-ileum-colon. That control is obtained by preferably restricting or preventing the flow of nutrients through the primary path while providing a secondary path for nutrients. The secondary path moves nutrients from the stomach directly to the small intestine and/or colon such that absorption of the nutrients is reduced.

Restriction of the flow of nutrients through the primary path may be controlled by any suitable technique or techniques. Although a device such as device 10 is most preferred, other techniques that may be used to restrict nutrient flow through the primary path include, but are not limited to, banding, surgical techniques, etc. at different points in the gastrointestinal system (e.g., in the stomach, at the pyloric sphincter, in the small intestine, etc.). Also, the methods and devices of the present invention may restrict nutrient flow through the pyloric sphincter—surgically and/or by other techniques. Techniques for restricting flow through the pyloric sphincter include those described earlier in this application with reference to describing the prior art.

b. Primary Path Flow Control

Figure 24:
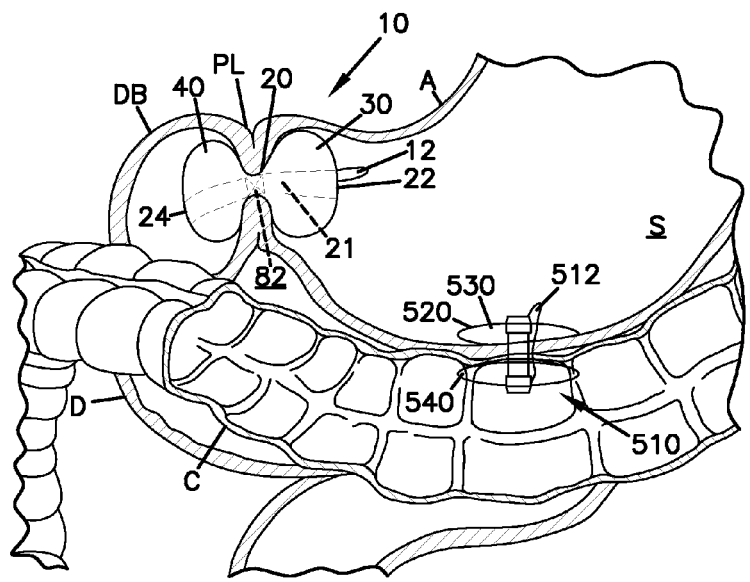
FIG. 24 depicts one exemplary embodiment of a treatment system including a primary gastric flow control device deployed in the pyloric sphincter and a secondary gastric flow control device deployed between the stomach and the colon.

FIG. 24 depicts two gastric flow control devices according to the present invention deployed within the gastrointestinal system of a patient. In the gastrointestinal deployment depicted in FIG. 1, a primary gastric flow control device 10 is such as that described above. In the embodiment shown, the device 10 includes a valve (such as that described with reference to FIG. 19).

c. Secondary Path Flow Control

FIG. 24 also depicts one example of a secondary gastric flow control device 510 deployed within the gastrointestinal system of a patient. The secondary gastric flow control device 510 is deployed within the stomach of the patient such that a proximal portion of the device 510 is located within the stomach S and the distal portion of the device 510 is located within the colon C. The distal portion could have an optional extended sleeve in the colon C (such as sleeve 50 described with reference to FIG. 16).

The device 510 may be of similar construction to device 10 with modifications as will be described. The device 510 includes a passageway 520, first (or proximal) expandable chamber 530, and a second (or distal) expandable chamber 540.

As compared to the primary gastric flow control device 10, the secondary gastric flow control device 510 may preferably include expandable chambers 530, 540 that, upon expansion, form an elongated disc shape as opposed to a rounded ball shape of chambers 30, 40. The lower profile shape of the expandable chambers 520, 530 help prevent or reduce the likelihood of occlusion in the colon C and to allow gastric contents easy access to the passageway 520.

The diameter of the second expandable chamber 540 could be any size that would prevent the chamber 540 from passing through the entry incision. The depth of the chamber 540 may preferably be no more than 1-2 cm to prevent occlusion (i.e. extend no more than 1-2 cm into the colon).

The surface of the chamber 530 located on the gastric end of the device 510 may preferably be concave or funneled. Such a shape facilitates the flow of stomach contents to the colon.

In the depicted deployment, the passageway 520 bridges or passes through an anastomosis created between the stomach S and the colon C. The proximal expandable chamber 530 is preferably located within the stomach. It may be preferred that the proximal expandable chamber 530 be positioned in the stomach proximate the location where the greater curve of the stomach approximates the transverse colon. The distal expandable chamber 540 is located within the colon. Similar to device 10, the device 510 also includes an expansion port 512 that may be used to expand the chambers 530, 540.

The secondary device 510 bridges an anastomosis created between the stomach and the colon. The secondary gastric control device 510 thus provides a secondary path through which nutrients can pass from the stomach to the colon, bypassing the small intestine.

It may be preferred that the secondary device 510 have a larger passageway 520 than the passageway 20 of the primary device 10. One potential result of providing secondary device 510 with a larger passageway than the primary device 10 is that, if the passageway 520 is open, a majority of ingested substances may be passed directly to the colon through secondary device 510.

The secondary gastric flow control device 510 may include a valve or valves as described above in connection with the primary gastric flow control device 10. In some instances, both the primary device 10 and the secondary device 510 may include valves. Typically, however, at least the secondary gastric flow control device will include a flow restriction valve that can be selectively open or restrict the size of the passageway as therapy would warrant. It may be preferred that the secondary gastric flow control device 510 include at least a one-way check valve to limit or prohibit the movement of colonic components into the stomach.

As an alternative (or in addition to) valves that can regulate flow, the secondary gastric flow control device 510 could be equipped with a cover, cap, lid, etc. to prevent or reduce the likelihood of contents passing into the colon from the stomach. These structures would preferably be located on the gastric side to allow the practitioner to (preferably endoscopically, remotely or by some other non-surgical technique) close the secondary gastric flow control device when the desired amount of weight has been lost. By maintaining the placement of the secondary device 510 (but not allowing any contents to flow therethrough) the incision would preferably be prevented from sealing over completely, thus avoiding the need to redeploy a secondary gastric flow control device in the event that the patient regains the lost weight. Alternatively, the device 510 could be plugged as described with reference to FIG. 15.

Either or both of the gastric flow control devices 10 and 510 may also be provided with filters on the gastric side of their respective passageways to prevent or reduce the likelihood of occlusion of the passage way by food particles. The filters may be provided in the form of, e.g., domed or tented screens on the gastric side of the channel to prevent occlusion by food particles or with raised rings as described with reference to FIG. 22.

Another optional feature that may be included in the secondary gastric flow control device is that the passageway 520 could be embedded with, or elute, an antibiotic agent to prevent or reduce the likelihood that colonic bacteria can migrate from the colon to the stomach.

d. Delivery of Artificial Fistula

Figure 25:
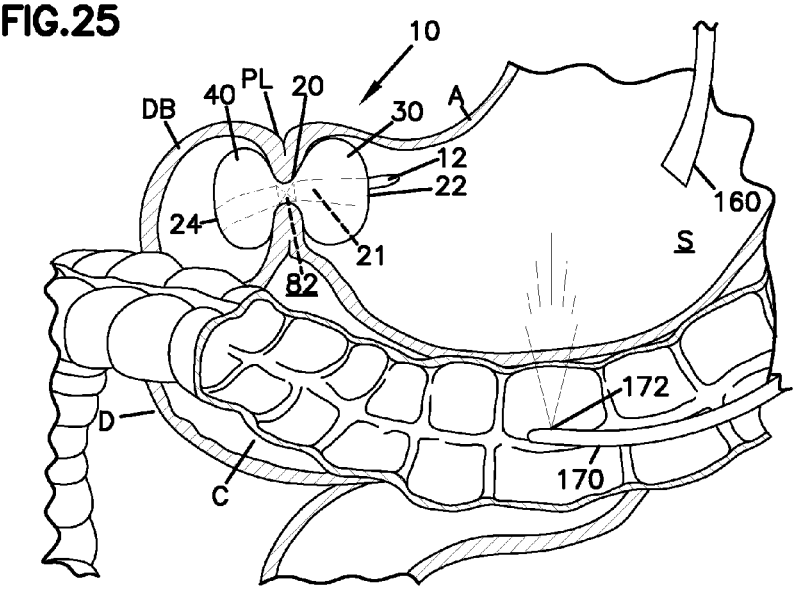
FIG. 25 is a view similar to FIG. 25 showing a deployed primary gastric flow control device a showing a first step in deploying a secondary gastric flow control device.
Figure 26:
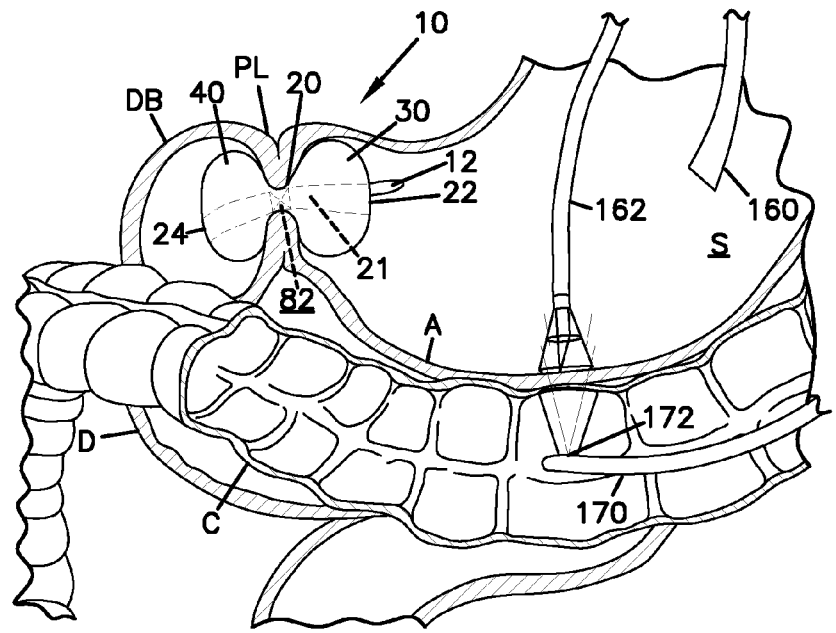
FIG. 26 is a view similar to FIG. 26 and showing a further step in deploying a secondary gastric flow control device.
Figure 27:
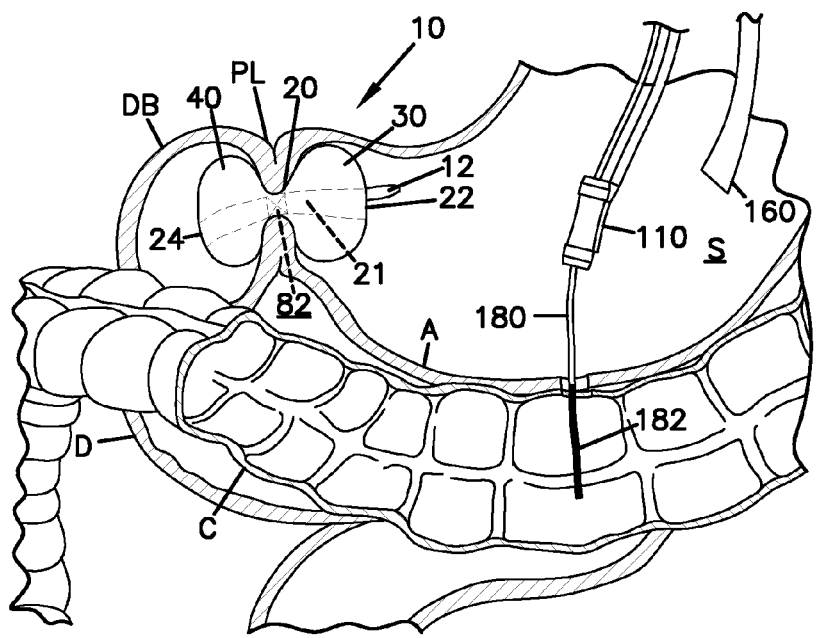
FIG. 27 is a view similar to FIG. 27 and showing a still further step in deploying a secondary gastric flow control device.

FIGS. 25-27 depict one method of deploying the secondary gastric flow control device 510. It may be preferred that the device 510 be deployed endoscopically using a combination of a gastroscope and colonoscope 170. The colonoscope 170 may preferably be equipped with a transillumination device 172 and inserted to the transverse colon. The gastroscope may preferably deliver a camera 160 to the stomach that would allow the operator to detect the light from the colonoscope 170 in the transverse colon.

In one alternative, two magnets (not shown, one attached to the gastroscope and one attached to the colonoscope) could be used to align the two scopes at the proper anatomic location and provide a defined point for placement. Another alternative method for placement of the gastric flow control device may involve the deployment of a balloon to the colon through the use of a colonoscope. The deployed balloon could be filled with, e.g., a contrast agent, air, etc. The balloon could be inflated to a diameter of, e.g., at least one but not more than five centimeters (to prevent perforation of the colon). Using ultrasonic energy, the practitioner could visualize the balloon in the colon and thereby determine the correct point of insertion of the secondary gastric flow control device.

Regardless of the placement method used, after a selected location for placement of the secondary gastric flow control device 510 has been identified, a junction or opening between the stomach S and the colon C at the selected location may preferably be formed using any suitable technique or techniques. In FIG. 26, an ablation tool 162 is deployed to create the desired junction between the stomach wall and the colonic wall at the selected location.

As depicted in FIG. 27, a needle 180 could preferably be used to pierce the walls of the stomach and colon at the selected location. A guidewire 182 could then be passed through the needle 180, and a tube passed over the guide wire. The tube may preferably contain a balloon to expand the opening between the stomach and the colon to allow for deployment of the secondary gastric flow control device 510.

It may be preferred that the secondary gastric flow control device 510 effectively creates an artificial gastrocolonic fistula. It may be preferred that the gastric and colonic walls be firmly attached and sealed together at the point of device placement to prevent or reduce the likelihood of gastric and colonic contents leaking into the peritoneal cavity and causing peritonitis. This attachment may preferably be maintained for at least one week (e.g., until scar tissue (fibrosis) forms to seal the incision points) and may preferably be maintained indefinitely.

The gastric wall-colonic wall junction could be maintained by the expandable chambers 530 and 540 in the device 510 alone. It may be preferred, for example, that the expandable chambers 530 and 540 be positioned such that full expansion of the chambers 530 and 540 may cause the chambers to touch or nearly touch each other such that complete closure of the gastric wall-colonic wall junction may be achieved.

Alternatively, sealing of the gastric wall-colonic wall junction could be accomplished using one or more of, e.g., magnets, clamps, clips, staples, adhesives, etc, alone or in combination with pressure provided by the chambers 530 and 540 of device 510. The techniques (if any) used to supplement the sealing provided by chambers 530 and 540 could be maintained indefinitely or could be made to degrade at a defined rate (biodegradable, pH sensitive, etc.).

e. Alternative Embodiments i. Alternative Structure

Figure 28:
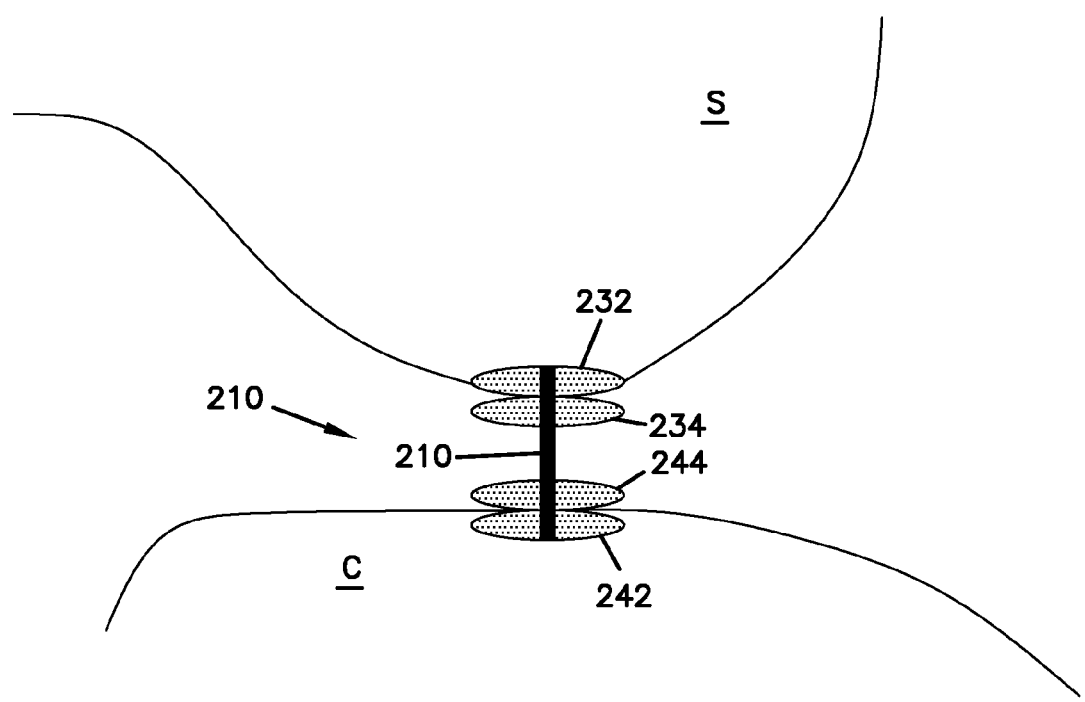
FIG. 28 depicts an alternative secondary gastric flow control device that may be used in connection with the present invention.

FIG. 28 schematically depicts one alternative secondary gastric flow control device 610. The device 610 may preferably be deployed in the same locations as the device 610 described above. One difference in the devices, however, is that device 610 includes a pair of expandable chambers 632 and 634 on one end and a pair of expandable chambers 642 and 644 on the opposite end of a passage 620. The chambers 634 and 644 on the peritoneal side of each opening may preferably help seal the incisions and keep the passageway 620 from migrating. The passageway 620 may preferably be of any selected length and may preferably have some flexibility to allow for independent movement of the stomach and colon.

ii. Fistula to Small Intestine

Although the secondary gastric flow control devices 510 and 610 are described as being deployed to provide a passageway between the stomach and the colon, the secondary gastric flow control devices used in connection with the present invention may alternatively provide a path from the stomach into the small intestine. If so deployed, it may be preferred that the secondary gastric flow control device provide a passage from the stomach into the jejunem.

Deployment of a secondary gastric flow control device into the small intestine may include, e.g., passing a needle through a gastroscope and piercing the wall of the stomach and the wall of the small intestine with the needle. Contrast solution could then be inserted to the region of small intestine and visualized by ultrasound. If the placement of the needle is not in the desired region of the small intestine the needle could be removed and inserted into a different area of the small intestine. Once the needle is in the correct position a guide wire could be passed through the needle and a tube could be passed over the guide wire. The tube may preferably contain a retracting structure to deploy within the small intestine, allowing the practitioner to pull the small bowel into contact with the stomach. The retracting structure could be in the form of, e.g., a T clip, a claw, a hook, an expandable bulb/disc, etc. Once the stomach and small intestine are positioned next to each other, a secondary gastric flow control device could be deployed in a similar manner as described above for the colonic devices.

In addition to, or in place of, the techniques described herein for creating passages between the stomach and colon or small intestine, other methods of creating anastomoses are known, e.g., surgical techniques, the laparoscopic/endoscopic techniques described in, e.g., U.S. Pat. No. 5,330,486 (Wilk), etc.

The devices of the present invention may preferably be adapted for delivery into the gastrointestinal system endoscopically, although other placement techniques and methods may also be possible. A variety of different delivery methods and structures may be described in, e.g., U.S. Pat. Nos. 4,315,509 (Smit); 4,501,264 (Rockey); and 5,306,300 (Berry); as well as U.S. Patent Publication No. US 2003/0040804 A1 (Stack et al.).

D. Single or Coordinated Therapy

The pyloric narrowing of device 10 is an independent therapy for reasons already discussed. Similarly, device 110, forming an artificial fistula between the stomach and intestines, is an independent therapy. Fistulas between the stomach and colon (referred to as "gastrocolic fistula") are rare but known. Such fistula are associated with significant weight loss since nutrients bypass the absorptive lengths of the small intestine. Such fistula are described in the following articles: Pitsinis, et al., "Gastrocolic Fistula as a Complication of Percutaneous Endoscopic Gastrostomy", *European Journal of Clinical Nutrition*, Vol. 57, pp. 876-878 (2003); Thyssen, et al., "Medical Treatment of Benign Gastrocolic Fistula", *Annals of Internal Medicine*, Vol. 118, No. 6, pp. 433-435 (1993); Cennamo, et al., "A Rare Gastric Ulcer Complication: the Gastrocolic Fistula. A Case Report.", Chir. Ital., Vol. 53, No. 6, pp. 869-872 (2001); Wagtmans, et al., "Persistent Diarrhoea in Cholecystocolic and Gastrocolic Fistula after Gastric Surgery", *Neth. J. Med.*, pp. 218-221 (December 1993) and Tavenor, et al., "Gastrocolic Fistula: A Review of 15 Cases and an Update of the Literature", *J. Clin. Gastroenterol.*, pp. 189-191 (April 1993).

The use of device 510 permits attaining weight loss through such a fistula in a manner which controls the fistula. The device could be used to provide a rapid weight loss. As an independent therapy, the device 510 can be used as a bridge to a more invasive bariatric surgery. For example, some patients may not be candidates for a Roux-en-Y procedure due to surgical risks associated with their very high body mass index. The device 510 can be applied in a less invasive procedure and permit a rapid weight loss to a point the patient is an acceptable candidate for the Roux-en-Y.

In combination with the device 10, the device 510 can be used as a rabid weight loss. Then, device 510 can be plugged or removed with device 10 used to maintain a lower weight.

With the device 510, a patient may preferably be instructed to drink electrolyte-rich solutions. Such solutions are commonly used in the treatment of cholera. Also, it may be advisable to treat such patients with drugs to reduce stomach acid production.

As used herein and in the appended claims, the singular forms "a," "and," and "the" include plural unless explicitly limited to the singular form or the context clearly dictates otherwise.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

We claim:

1. An apparatus for creating a fistula between a stomach and an intestine of a patient, said apparatus comprising
    a flow controller for creating a fistula from said stomach to said intestine of said patient comprising:
    a) a passageway having an internal lumen with an inlet end and an outlet end, said passageway sized to extend from said stomach to said intestine with said inlet residing in said stomach and with said outlet residing in said intestine, and having a valve for controlling the flow of contents through the passageway;
    b) a first expandable chamber attached to the passageway proximate said inlet; and
    c) second expandable chamber attached to the passageway proximate said outlet; wherein said first and second chambers are adapted to seal against opposing tissue of at least one of said stomach and said intestine upon expansion of said chambers; and d) an anchor for securing the passageway, wherein said passageway is completely outside the pylorus.

2. An apparatus of claim 1, further comprising an anchor for securing the passageway at the inlet end or at the outlet end.

3. An apparatus according to claim 2, wherein the anchor is selected from the group consisting of magnets, clamps, clips, staples and adhesives.

4. An apparatus according to claim 2, wherein said anchor comprises:
   f) a third expandable chamber attached to the passageway proximate said inlet; and
   g) a fourth expandable chamber attached to the passageway proximate said outlet; wherein said first and third chambers and said second and fourth chambers are adapted to form first and second cooperating pairs upon expansion for a stomach wall to be captured between said first pair of chambers, and with an intestine wall captured between said second pair of chambers.

5. An apparatus according to claim 1, wherein said valve is a one way valve.

6. An apparatus according to claim 1, wherein said valve is a flow restriction valve.

7. An apparatus according to claim 1, further comprising an injection port for inflating first or second inflatable chambers.

8. An apparatus according to claim 5, wherein the first and second inflatable chambers can be inflated with a liquid or a gas.

9. An apparatus according to claim 4, further comprising an injection port for inflating third or fourth inflatable chambers.

10. An apparatus according to claim 9, wherein the third and fourth inflatable chambers can be inflated with a liquid or a gas.

11. An apparatus according to claim 1, wherein the said outlet end comprises a sleeve.

12. An apparatus according to claim 1, wherein the passageway is adapted to elute an antimicrobial agent.

13. An apparatus according to claim 1, wherein the inlet end comprises a cover to prevent flow of contents from the stomach into the intestine.

14. A method of positioning an apparatus according to claim 1 comprising:
   a) administering a gastroscope to a patient;
   b) administering a colonscope to the patient, wherein the colonscope has a detectable component;
   c) detecting the detectable component of the colonscope to identify a point of placement;
   d) forming an opening at the point of placement;
   e) delivering the apparatus of claim 1 to the point of placement;
   f) and expanding the first and second chambers.

15. The method of claim 14, wherein the detectable component of the colonscope is a light.

16. The method of claim 14, wherein the detectable component of the colonscope is a detectable balloon.

17. The method of claim 16, wherein the balloon contains a contrast agent.

18. The method of claim 14, wherein the detectable component of the colonscope is a magnet and the gastroscope comprises a magnet.

19. The method of claim 14, wherein the opening is formed at the point of placement using a needle.

20. The method of claim 19, wherein the opening is formed by enlarging the opening made by the needle with a balloon.

21. The method of claim 14 wherein the apparatus of claim 1 is delivered by an endoscope.

22. The method of claim 14, wherein the chambers are expanded by delivering a fluid through an injection port.

23. A method of positioning an apparatus according to claim 1 comprising:
   g) administering a gastroscope to a patient;
   h) administering a colonscope to the patient, wherein the colonscope has a detectable component;
   i) detecting the detectable component of the colonscope to identify a point of placement;
   j) forming an opening at the point of placement;
   k) delivering the apparatus of claim 4 to the point of placement;
   l) and expanding the first, second, third, and fourth chambers.

* * * * *

UNITED STATES PATENT AND TRADEMARK OFFICE
CERTIFICATE OF CORRECTION

| | |
|---|---|
| PATENT NO. | : 8,372,158 B2 |
| APPLICATION NO. | : 12/887714 |
| DATED | : February 12, 2013 |
| INVENTOR(S) | : Michael J. Levy et al. |

Page 1 of 1

It is certified that error appears in the above-identified patent and that said Letters Patent is hereby corrected as shown below:

Title Page: Item (73) the Assignee should read: Mayo Foundation for Medical Education and Research Signed and Sealed this
Tenth Day of December, 2013

Margaret A. Focarino
*Commissioner for Patents of the United States Patent and Trademark Office*